US010967078B2

(12) United States Patent
Van Gool et al.

(10) Patent No.: US 10,967,078 B2
(45) Date of Patent: Apr. 6, 2021

(54) RADIOLABELLED MGLUR2 PET LIGANDS

(71) Applicant: Janssen Pharmaceutica NV, Beerse (BE)

(72) Inventors: Michiel Luc Maria Van Gool, Madrid (ES); José Ignacio Andrés-Gil, Madrid (ES); Manuel Jesús Alcázar-Vaca, Toledo (ES); Guy Maurits R. Bormans, Rotselaar (BE); Sofie Jeanne Leopoldine Celen, Tessenderlo (BE); Joost Verbeek, Enkhuizen (NL)

(73) Assignee: JANSSEN PHARMACEUTICA NV, Beerse (BE)

( * ) Notice: Subject to any disclaimer, the term of this patent is extended or adjusted under 35 U.S.C. 154(b) by 141 days.

(21) Appl. No.: 15/533,279

(22) PCT Filed: Dec. 2, 2015

(86) PCT No.: PCT/EP2015/078296
§ 371 (c)(1),
(2) Date: Jun. 5, 2017

(87) PCT Pub. No.: WO2016/087489
PCT Pub. Date: Jun. 9, 2016

(65) Prior Publication Data
US 2018/0264147 A1  Sep. 20, 2018

(30) Foreign Application Priority Data

Dec. 3, 2014 (EP) .................................. 14196081

(51) Int. Cl.
| | | |
|---|---|---|
| A61K 51/00 | (2006.01) | |
| A61M 36/14 | (2006.01) | |
| A61K 51/04 | (2006.01) | |
| A61P 25/18 | (2006.01) | |
| A61P 25/24 | (2006.01) | |
| C07B 59/00 | (2006.01) | |
| C07D 419/14 | (2006.01) | |
| C07D 487/04 | (2006.01) | |
| A61B 6/03 | (2006.01) | |
| C07K 14/705 | (2006.01) | |

(52) U.S. Cl.
CPC .......... A61K 51/0459 (2013.01); A61P 25/18 (2018.01); A61P 25/24 (2018.01); C07B 59/002 (2013.01); C07D 419/14 (2013.01); C07D 487/04 (2013.01); A61B 6/037 (2013.01); A61K 2123/00 (2013.01); C07B 2200/05 (2013.01); C07K 14/70571 (2013.01)

(58) Field of Classification Search
CPC .......... A61P 25/18; A61P 25/24; A61P 6/037; A61P 2123/00; A61P 51/0459; C07B 59/002; C07B 2200/05; C07D 419/14; C07D 487/04; A61B 6/037; A61K 2123/00; C07K 14/70571

USPC ......................................................... 424/1.89
See application file for complete search history.

(56) References Cited

U.S. PATENT DOCUMENTS

| | | |
|---|---|---|
| 7,361,659 B2 | 4/2008 | Gatti McArthur et al. |
| 7,378,417 B2 | 5/2008 | Goetschi et al. |
| 7,514,443 B2 | 4/2009 | Wichmann et al. |
| 2001/0011087 A1 | 8/2001 | Wehner et al. |
| 2003/0027807 A1 | 2/2003 | Wehner et al. |
| 2005/0107412 A1 | 5/2005 | Maw et al. |
| 2013/0310555 A1 | 11/2013 | Chong |

FOREIGN PATENT DOCUMENTS

| | | |
|---|---|---|
| EP | 0756200 | 1/1997 |
| EP | 2327704 | 6/2011 |
| EP | 2666775 | 11/2013 |
| JP | 2007507446 | 3/2007 |
| JP | 2008503510 | 2/2008 |
| JP | 2008530042 | 8/2008 |
| JP | 2013189395 | 9/2013 |
| WO | 2002/096873 | 12/2002 |
| WO | 2005/002552 | 1/2005 |
| WO | 2005/061507 | 7/2005 |
| WO | 2006/030847 | 3/2006 |
| WO | 2006/050803 | 5/2006 |
| WO | 2007/084314 | 7/2007 |
| WO | 2007/092416 | 8/2007 |
| WO | 2008/001115 | 1/2008 |
| WO | 2008/141239 | 11/2008 |
| WO | 2009/095872 | 8/2009 |
| WO | 2009/118292 | 10/2009 |

(Continued)

OTHER PUBLICATIONS

Andres et al. J. Med. Chem. 2012, 55, 8685-8699.*
Cai et al. Eur. J. Org. Chem. 2008 2853-2873.*
Suzuki et al. Chem. Eur. J. 1997, 2039-2042.*
Malkov et al. J. Org. Chem. 2009, 74, 8425-8427.*
International Search Report re: PCT/EP2015/078296 dated Feb. 19, 2016.
International Search Report re: PCT/EP2015/078285 dated Feb. 1, 2016.
International Search Report re: PCT/EP2015/079216 dated Feb. 25, 2016.

(Continued)

*Primary Examiner* — Michael G. Hartley
*Assistant Examiner* — Sean R Donohue
(74) *Attorney, Agent, or Firm* — Fay Kaplun & Marcin, LLP

(57) ABSTRACT

The present invention relates to novel, selective, radiolabelled mGluR2 ligands which are useful for imaging and quantifying the metabotropic glutamate receptor mGluR2 in tissues, using positron-emission tomography (PET). The invention is also directed to compositions comprising such compounds, to processes for preparing such compounds and compositions, to the use of such compounds and compositions for imaging a tissue, cells or a mammal, in vitro or in vivo and to precursors of said compounds.

2 Claims, 4 Drawing Sheets

(56) References Cited

FOREIGN PATENT DOCUMENTS

| WO | 2009/130232 | 10/2009 |
|---|---|---|
| WO | 2010/130424 | 11/2010 |
| WO | 2010130424 | 11/2010 |
| WO | 2012/035078 | 3/2012 |
| WO | 2012062752 A1 | 5/2012 |
| WO | 2012/083224 | 6/2012 |
| WO | 2012/143726 | 10/2012 |
| WO | 2013/012915 | 1/2013 |
| WO | 2013/012918 | 1/2013 |
| WO | 2013066736 A1 | 5/2013 |
| WO | 2013/154878 | 10/2013 |
| WO | 2013/156869 | 10/2013 |
| WO | 2013174822 | 11/2013 |
| WO | 2013/192343 | 12/2013 |
| WO | 2013/192347 | 12/2013 |
| WO | 2013/192350 | 12/2013 |
| WO | 2014008197 A1 | 1/2014 |
| WO | 2014064028 A1 | 5/2014 |
| WO | 2014195311 A1 | 12/2014 |
| WO | 2016/016380 | 2/2016 |
| WO | 2016/016381 | 2/2016 |
| WO | 2016/016382 | 2/2016 |
| WO | 2016/016383 | 2/2016 |
| WO | 2016/016395 | 2/2016 |
| WO | 2016/087487 | 6/2016 |
| WO | 2016/087489 | 6/2016 |
| WO | 2017/103179 | 6/2017 |
| WO | 2017/103182 | 6/2017 |

OTHER PUBLICATIONS

Alfonso R Gennaro, 18th edition Remington's—Pharmaceutical Sciences, 18th edition Remington's—Pharmaceutical Sciences, 1990, Part 8_ Pharmaceutical preparations and their Manufacture_ pp. 1435-1714, Part 8.
Alper R. et al, Agonist-Stimulated [35S]GTBgS Binding, Current Protocols in Pharmacology, 1998, suppl.2,.
Anonymous, A study to assess the relative bioavailability of TMC207 Following single-dose administrations of two pediatric formulations in healthy adult participants, /, Mar. 2014,1, /, /.
Celia Goeldner, Cognitive impairment in major depression and the mGlu2 receptor as a therapeutic target, Neuropharmacology, Aug. 3, 2013, pp. 337-346, 64.
Cid Jose Maria et al, Discovery of 3-Cyclopropylmethyl-7-(4-phenylpiperidin-1-yl)-8-trifluoromethyl[1,2,4]triazolo[4,3-a]pyridine (JNJ-42153605): A Positive Allosteric Modulator of the Metabotropic Glutamate 2 Receptor, Journal of Medicinal Chemistry, Oct. 16, 2012, pp. 8770-8789, 55.
Ferraguti,et al, Metabotropic glutamate receptors, Cell & Tissue Research, Jul. 18, 2006, pp. 483-504, 326.
Hiroyuki Koike et al, Role of BDNF/TrkB signaling in antidepressant-like effects of a group II metabotropic glutamate receptor antagonist in animal models of depression, Behavioural Brain Research, Oct. 23, 2012, pp. 48-52, 238.
Kelmendi et al, The role of the Glutamatergic system in the pathophysiology and treatment of mood disorders, Primary Psychiatry, Oct. 2006, pp. 80-86, vol. 13 No. 10.
Lynne Gilfillian et al, Synthesis and biological evaluation of novel 2,3-dihydro-1H-1,5-benzodiazepin-2-ones; potential imaging agents of the metabotropic glutamate 2 receptor, Med. Chem. Commun., May 29, 2013, 1118-1123, 4.
Niswender Colleen M. et al, Metabotropic Glutamate Receptors: Physiology, Pharmacology, and Disease, Annu.Rev.Pharmacol. Toxicol., 2010, pp. 295-322, 50.
Schaffhauser et al, Pharmacological Characterization and Identification of Amino Acids Involved in the Positive Modulation of Metabotropic Glutamate Receptor Subtype 2, Molecular Pharmacology, Jun. 13, 2003, pp. 798-810, vol. 64, No. 4.
Bigotti et al., "Synthesis of Ψ[CH(RF) NH]Gly-peptides: the dramatic effect of a single fluorine atom on the diastereocontrol of the key aza-Michael reaction", J. Fluorine Chem., vol. 129, Issue 9, Sep. 2008, pp. 767-774.
Hoffmann-La Roche, ClinicalTrials.gov Identifier NCT01457677, Nov. 2016, 6 sheets.
Bell, "DSM-IV: Diagnostic & Statistical Manual of Mental Disorders", JAMA., vol. 272, No. 10, Sep. 1994, pp. 828-829.
Dinklo et al, "Characterization of 2-[[4-Fluoro-3-(trifluoromethyl)phenyl]amino-4-(4-pyridinyl)-5-thiazolemethanol (JNJ-1930942), a Novel Positive Allosteric Modulator of the α7 Nicotinic Acetylcholine Receptor", J. Pharmacol. Exp. Ther., vol. 336, No. 2, Feb. 2011, pp. 560-574.
Embrechts et al,. "Longitudinal characterisation of the TauPS2APP mouse model of Alzheimer's disease in a two trial discrimination task of visuo-spatial recognition memory", 45th European Brain and Behaviour Society Meeting, Sep. 2013, p. 202.
Ermolat'ev et al., "One-pot microwave-assisted protocol for the synthesis of substituted 2-amino-1H-imidazoles", Molecular Diversity, vol. 15, No. 2, May 2011, pp. 491-496.
Hackam et al., "Translation of research evidence from animals to humans", JAMA, vol. 296, No. 14, Oct. 2006, pp. 731-732.
Hickinbottom, English translation of the relevent from reaction of organic complonents, Reactions of organic compounds, 1939, pp. 360-362.
Higgins et al., "Pharmacological manipulation of mGlu2 receptors influences cognitive performance in rodents", Neuropharmacology, vol. 46, May 2004, pp. 907-917.
Int. search report for PCT/EP2014/061478—JAB6015.
Int. search report for PCT/EP2015/067530—JAB6033.
Int. search report for PCT/EP2015/067533—JAB6034.
Int. search report for PCT/EP2015/067534—JAB6036.
Int. search report for PCT/EP2015/067538—JAB 6037.
Int. search report for PCT/EP2015/067572—JAB6035.
Jordan, "Tamoxifen: A Most Unlikely Pioneering Medicine", Nature Reviews Drug Discovery, vol. 2, Mar. 2003, pp. 205-213.
Li et al., "Palladium-Catalyzed Oxidative Rearrangement of Tertiary Allylic Alcohols to Enones with Oxygen in Aqueous Solvent", Organic Letters, No. 16, Oct. 2014, pp. 5370-5373.
Shigemoto et al., "Differential Presynaptic Localization of Metabotropic Glutamate Receptor Subtypes in the Rat Hippocampus", the Journal of Neuroscience, vol. 17, issue 19, Oct. 1997, pp. 7503-7522.
Vippagunta et al, "Crystalline solids", Advanced Drug Delivery Reviews, vol. 48, Issue 1, May 2001, pp. 3-26.
Knunyantz et al., English translation of the relevant parts from 'Khumicheskaya encyclopedia, vol. 1, Moscow, 1988, pp. 242-243.
Sheffler et al., "Recent Progress in the Synthesis and Characterization of Group II Metabotropic Glutamate Receptor Allosteric Modulators", ACS Chemical Neuroscience, vol. 2, Apr. 2011, pp. 382-393.

* cited by examiner

Fig. 1

WT-TB (tracer) ID:9    WT-TB (tracer) ID:10    WT-TB (tracer) ID:11    KO-TB (tracer) ID:16    KO-TB (tracer) ID:17    KO-TB (tracer) ID:18

WT-AS ID:12 (tracer + Co. No. 1)    WT-AS ID:13 (tracer + Co. No. 1)    KO-AS ID:19 (tracer + Co. No. 1)    KO-AS ID:20 (tracer+Co. No. 1)

Fig. 2

WT-TB (tracer) Mouse '1', ID:1    WT-TB (tracer) Mouse '1', ID:2    WT-TB (tracer) Mouse '2', ID:1    KO-TB (tracer) Mouse '3', ID:1    KO-TB (tracer) Mouse '3', ID:2    KO-TB (tracer) Mouse '1', ID:1

Non-specific 10 µM Co. No. 1

WT-AS Mouse '1', ID:3 (tracer + Co. No. 1)    WT-AS Mouse '2', ID:2 (tracer + Co. No. 1)    KO-AS Mouse '3', ID:3 (tracer + Co. No. 1)    KO-AS Mouse '1', ID:2 (tracer+Co. No. 1)

RADIOLABELLED MGLUR2 PET LIGANDS

CROSS REFERENCE TO RELATED APPLICATIONS

This application is the national stage of PCT Application No. PCT/EP2015/078296, filed Dec. 2, 2015, which claims priority from European Patent Application No. 14196081.5, filed Dec. 3, 2014, the entire disclosures of which are hereby incorporated in their entirety.

FIELD OF THE INVENTION

The present invention relates to novel, selective, radiolabelled mGluR2 ligands which are useful for imaging and quantifying the metabotropic glutamate receptor mGluR2 in tissues, using positron-emission tomography (PET). The invention is also directed to compositions comprising such compounds, to processes for preparing such compounds and compositions, to the use of such compounds and compositions for imaging a tissue, cells or a mammal, in vitro or in vivo and to precursors of said compounds.

BACKGROUND OF THE INVENTION

The glutamatergic system in the CNS is one of the neurotransmitter systems that play a key role in several brain functions. Metabotropic glutamate receptors (mGluR) belong to the G-protein-coupled family, and eight different subtypes have been identified to date, which are distributed to various brain regions (Ferraguti & Shigemoto, Cell & Tissue Research, 326:483-504, 2006). mGluRs participate in the modulation of synaptic transmission and neuronal excitability in the CNS by the binding of glutamate. This activates the receptor to engage intracellular signaling partners, leading to cellular events (Niswender & Conn, Annual Review of Pharmacology & Toxicology 50:295-322, 2010).

mGluRs are further divided into three subgroups based on their pharmacological and structural properties: group-I (mGluR1 and mGluR5), group-II (mGluR2 and mGluR3) and group-III (mGluR4, mGluR6, mGluR7 and mGluR8). Group-II ligands, both orthosteric and allosteric modulating, are considered to be potentially useful in the treatment of various neurological disorders, including psychosis, mood disorders, Alzheimer's disease and cognitive or memory deficiencies. This is consistent with their primary localisation in brain areas such as the cortex, hippocampus and the striatum (Ferraguti & Shigemoto, Cell & Tissue Research 326:483-504, 2006). Particularly antagonists and negative allosteric modulators are reported to hold potential for the treatment of mood disorders and cognitive or memory dysfunction. This is based on findings with group-II receptor antagonists and negative allosteric modulators tested in laboratory animals subjected to a range of experimental conditions deemed relevant to these clinical syndromes (Goeldner et al, Neuropharmacology 64:337-346, 2013). Clinical trials are, for example, underway with mGluR2/3 antagonist RO4995819 (F. Hoffmann-La Roche Ltd.) in adjunctive therapy in patients with Major Depressive Disorder having inadequate response to ongoing antidepressant treatment (ClinicalTrials.gov Identifier NCT01457677, retrieved 19 Feb. 2014). WO 2013066736 (Merck Sharp & Dohme Corp.) describes quinoline carboxamide and quinoline carbonitrile compounds as mGluR2 NAMs. WO2013174822 (Domain therapeutics) describes 4H-pyrazolo[1,5-a]quinazolin-5-ones and 4H-pyrrolo[1,2-a]quinazolin-5-ones and in vitro mGluR2 NAM activity thereof. WO 2014064028 (F. Hoffman-La Roche AG) discloses a selection of mGlu2/3 negative allosteric modulators and their potential use in the treatment of Autistic Spectrum Disorders (ASD).

The group-II receptors are mainly located on presynaptic nerve terminals where they exert a negative feedback loop to the release of glutamate into the synapse (Kelmendi et al, Primary Psychiatry 13:80-86, 2006). Functional inhibition of these receptors by antagonists or negative allosteric modulators therefore lifts the brake on glutamate release, resulting in enhanced glutamatergic signaling. This effect is believed to underlie the antidepressant-like and procognitive effects observed in preclinical species with inhibitors of the Group-II receptor. In addition, treatment of mice with group-II orthosteric antagonists has been shown to enhance signaling by growth factors such as brain derived neurotrophic factor (BDNF) (Koike et al, Behavioural Brain Research 238:48-52, 2013). Since BDNF and other growth factors have been shown to be critically involved mediating synaptic plasticity, this mechanism is likely to contribute to both antidepressant and procognitive properties of these compounds. Inhibition of mGluRs of the group-II receptor family is therefore considered to represent a potential therapeutic mechanism for neurological disorders, including depression and cognitive or memory dysfunction.

Positron Emission Tomography (PET) is a non-invasive imaging technique that offers the highest spatial and temporal resolution of all nuclear imaging techniques and has the added advantage that it can allow for true quantification of tracer concentrations in tissues. It uses positron emitting radionuclides such as, for example, $^{15}O$, $^{13}N$, $^{11}C$ and $^{18}F$ for detection. Several positron emission tomography radiotracers have been reported so far for in vivo imaging of mGluRs. There is still a need to provide improved positron emission tomography radiotracers for imaging mGluR2.

SUMMARY OF THE INVENTION

The present invention relates to a compound having the Formula (I)

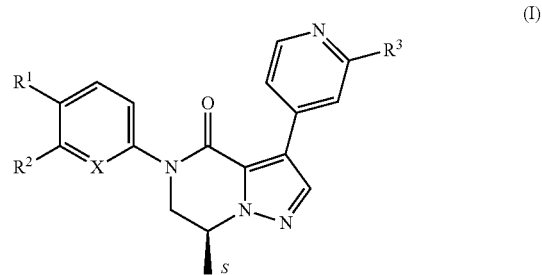

wherein,
X is CH or N,
$R^1$ is selected from the group of $CF_3$, $SF_5$, and Cl;
$R^2$ is selected from the group of H, Cl, and —$OCH_3$; and
$R^3$ is selected from —$NHCH_3$, $CH_3$, and F;
wherein at least one atom is radiolabelled, or a pharmaceutically acceptable salt or a solvate thereof.

The invention also relates to precursor compounds for the synthesis of a compound of Formula (I) as previously defined. Thus, the present invention also relates to compounds of Formulae (P-I), (P-II), or (P-III)

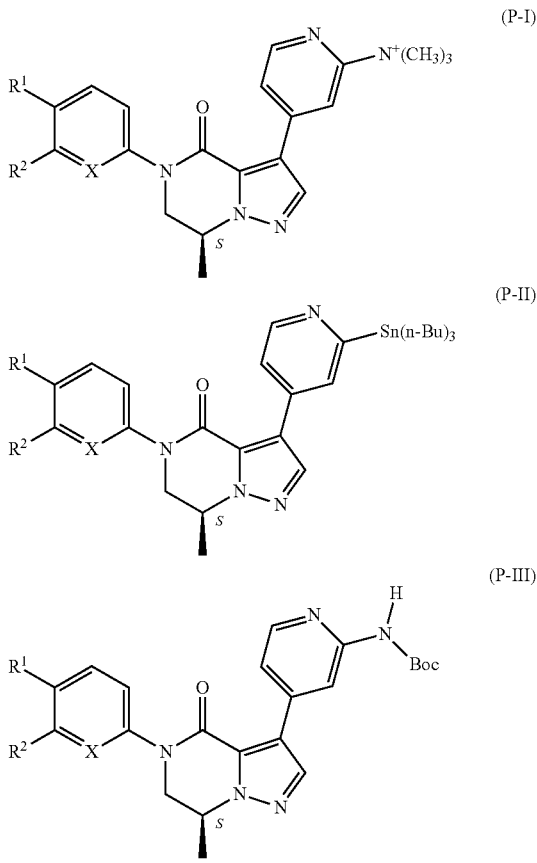

wherein
X is CH or N,
R¹ is selected from the group of $CF_3$, $SF_5$, and Cl;
R² is selected from the group of H, Cl, and —$OCH_3$; and
Boc is tert-butyloxycarbonyl.

The invention also relates to reference materials, corresponding for example, to the corresponding [$^{12}$C]-compounds or the [$^{19}$F]-compounds of Formula (I). In an additional aspect, the invention relates to the compound

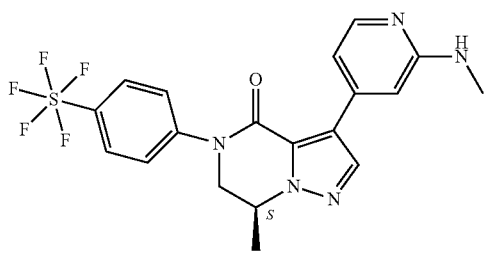

or a pharmaceutically acceptable salt or a solvate thereof.

The invention also relates to a pharmaceutical composition comprising a compound of Formula (I) or a pharmaceutically acceptable salt thereof and a pharmaceutically acceptable carrier or diluent. In a particular embodiment, said pharmaceutical composition is particularly suitable for diagnosis and may be referred to therefore as a diagnostic pharmaceutical composition. In particular, said pharmaceutical composition is a sterile solution. Thus, illustrative of the invention is a sterile solution comprising a compound of Formula (I) described herein.

The invention further relates to the use of a compound of Formula (I) as an imaging agent. Therefore, exemplifying the invention is a use of a compound of Formula (I) as described herein, for, or a method of, imaging a tissue, cells or a mammal, in vitro or in vivo.

The invention also relates to a method for imaging a tissue, cells or a mammal, comprising contacting with or providing or administering a detectable amount of a labelled compound of Formula (I) as described herein to a tissue, cells or a mammal, and detecting the compound of Formula (I).

Further exemplifying the invention is a method of imaging a tissue, cells or a mammal, comprising contacting with or providing or administering to a tissue, cells or a mammal, a compound of Formula (I) as described herein, and imaging the tissue, cells or mammal with a positron-emission tomography imaging system. Additionally, the invention refers to a process for the preparation of a compound according to Formula (I) as described herein, comprising (a) the steps of reacting a compound according to Formula (P-III) as defined herein, with [$^{11}$C]$CH_3$I under appropriate conditions, followed by Boc cleavage under appropriate conditions,

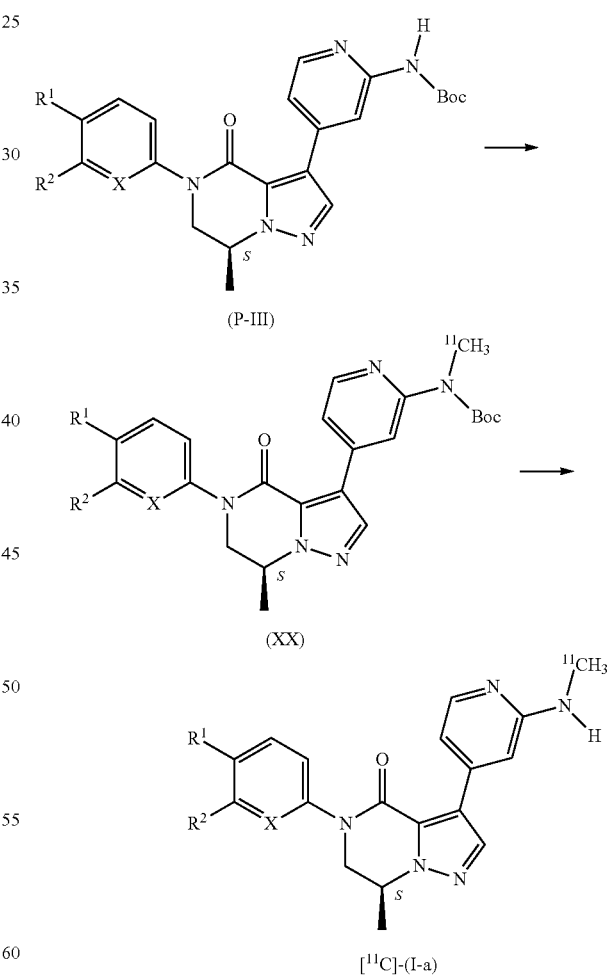

or
(b) the step of reacting a compound of Formula (P-I) as defined herein, with $^{18}$F⁻/4,7,13,16,21,24-hexaoxa-1,10-diazabicyclo[8.8.8]hexacosane in the presence of $K_2C_2O_4$ or $KHCO_3$,

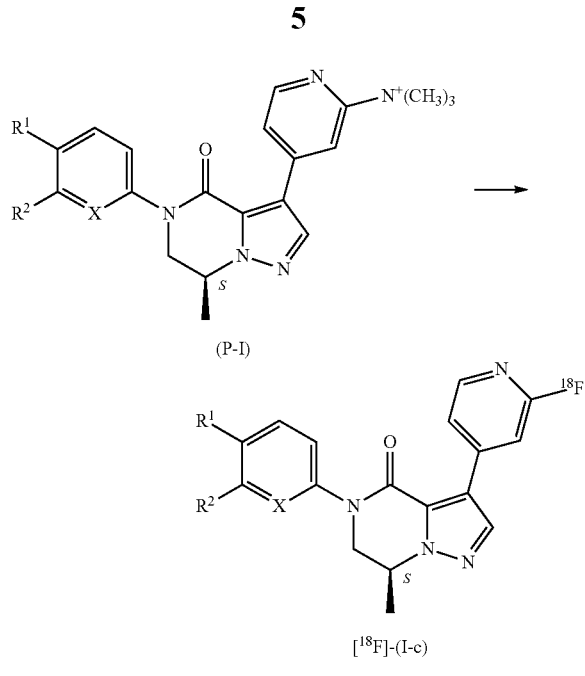

(P-I)

[$^{18}$F]-(I-c)

or
(c) the step of reacting a compound of Formula (P-II) as defined herein, with [$^{11}$C]CH$_3$I

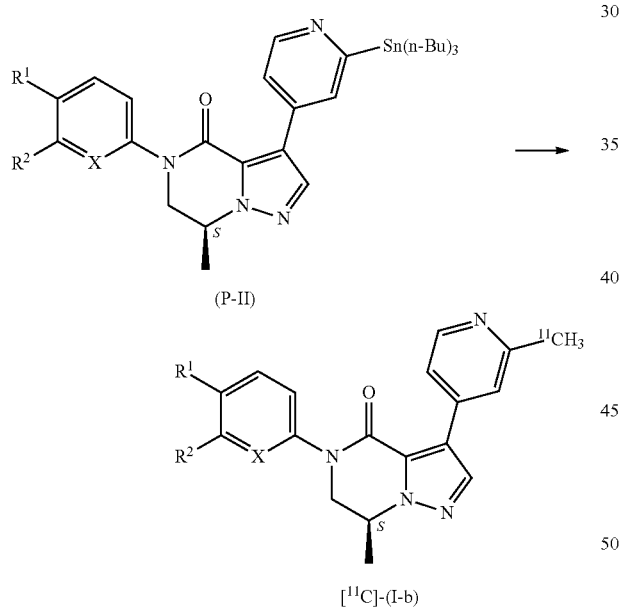

(P-II)

[$^{11}$C]-(I-b)

DESCRIPTION OF THE FIGURES

FIG. 1 shows the binding of [$^{11}$C]-2 to mGluR2 knockout (KO) and wild type (WT) mouse brain sections. TB=total tracer binding presented in the upper row; AS=a-specific binding in presence of 10 μM of Co. No. 1 presented in the lower row.

FIG. 2 shows the binding of [$^{11}$C]-1 to mGluR2 KO and WT mouse brain sections. TB=total tracer binding presented in the upper row; AS=a-specific binding in presence of 10 μM of Co. No. 1 presented in the lower row.

DETAILED DESCRIPTION OF THE INVENTION

Figure 3:
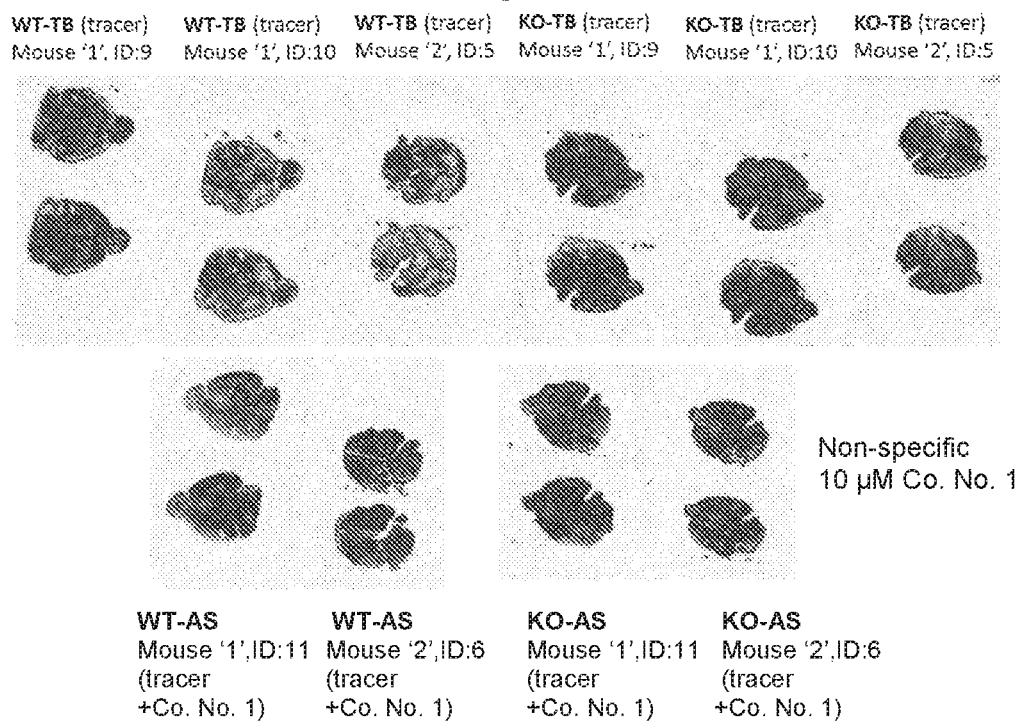
FIG. 3 shows the binding of [$^{18}$F]-3 to mGluR2 KO and WT mouse brain sections. TB=total tracer binding presented in the upper row; AS=a-specific binding in presence of 10 μM of Co. No. 1 presented in the lower row.
Figure 4:
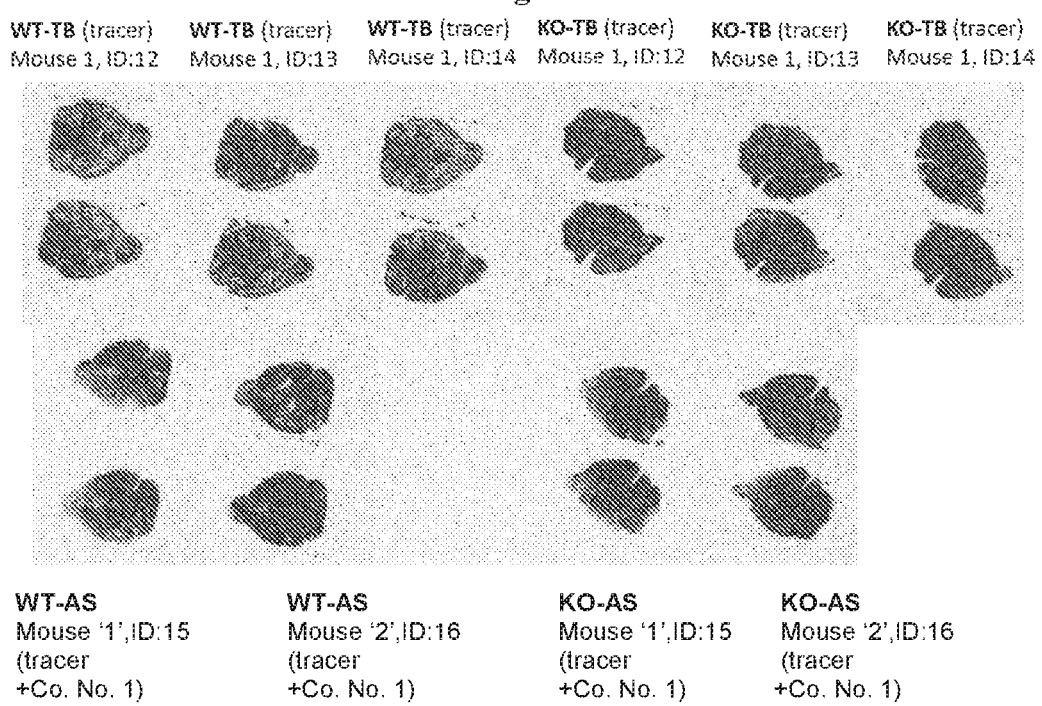
FIG. 4 shows the binding of [$^{11}$C]-5 to mGluR2 KO and WT mouse brain sections. TB=total tracer binding presented in the upper row; AS=a-specific binding in presence of 10 μM of Co. No. 1 presented in the lower row.
Figure 5:
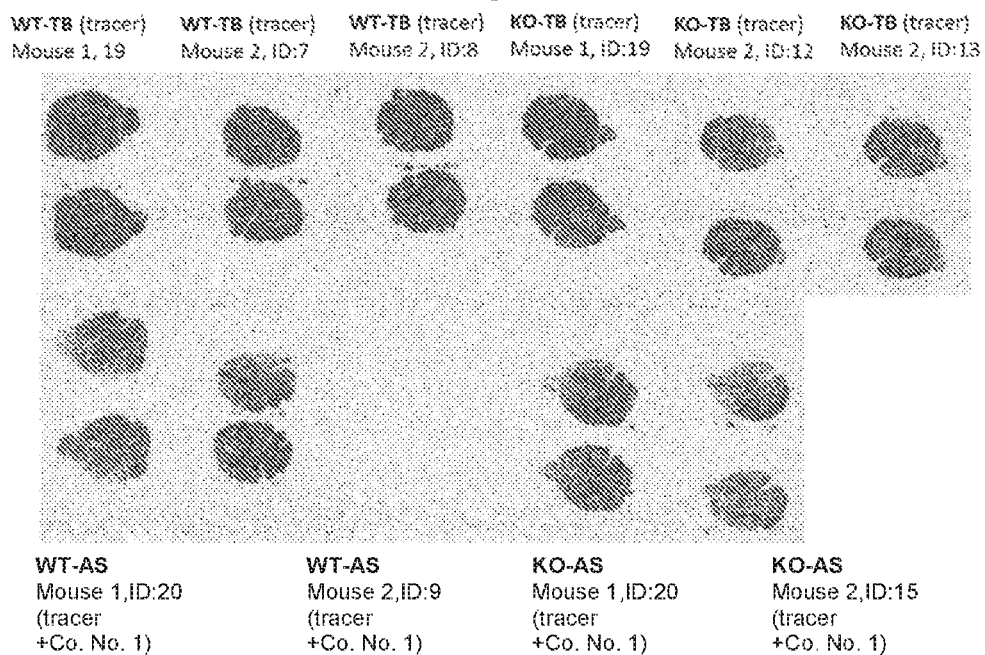
FIG. 5 shows the binding of [$^{11}$C]-4 to mGluR2 KO and WT mouse brain sections. TB=total tracer binding presented in the upper row; AS=a-specific binding in presence of 10 μM of Co. No. 1 presented in the lower row.

The present invention is directed to compounds of Formula (I) as defined hereinbefore, and pharmaceutically acceptable salts and the solvates thereof.

In one embodiment, the present invention relates to a compound of Formula (I), wherein

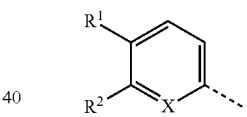

is selected from (a), (b), (c) or (d):

 (a)

 (b)

 (c)

 (d)

and R$^3$ is as defined herein, or a pharmaceutically acceptable salt or a solvate thereof.

In another embodiment of the present invention, $R^3$ is selected from

—NH[$^{11}$C]CH$_3$, [$^{11}$C]CH$_3$, and $^{18}$F.

In an additional embodiment of the present invention, the compound of Formula (I) is selected from a compound of Formula [$^{11}$C]-(I-a)

[$^{11}$C]-(I-a)

wherein

X, $R^1$ and $R^2$ are as defined herein, or a pharmaceutically acceptable salt or a solvate thereof.

In an additional embodiment of the present invention, the compound of Formula (I) is selected from a compound of Formula [$^{11}$C]-(I-a)

[$^{11}$C]-(I-a)

wherein is selected from (a), (b), or (c):

(a)

(b)

(c)

or a pharmaceutically acceptable salt or a solvate thereof.

Particular compounds of Formula [$^{11}$C]-(I-a) can be selected from [$^{11}$C]-2, [$^{11}$C]-5, or [$^{11}$C]-4:

[$^{11}$C]-2

[$^{11}$C]-4

[$^{11}$C]-5 or a pharmaceutically acceptable salt or a solvate thereof.

In an additional embodiment of the present invention, the compound of Formula (I) is selected from a compound of Formula [$^{11}$C]-(I-b)

[$^{11}$C]-(I-b)

wherein

X, $R^1$ and $R^2$ are as defined herein, or a pharmaceutically acceptable salt or a solvate thereof.

In an additional embodiment of the present invention, the compound of Formula [$^{11}$C]-(I-b) is [$^{11}$C]-1

[$^{11}$C]-1

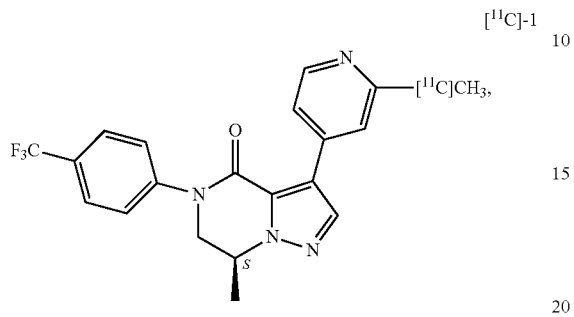

or a pharmaceutically acceptable salt or a solvate thereof.

In an additional embodiment of the present invention, the compound of Formula (I) is selected from a compound of Formula [$^{18}$F]-(I)

[$^{18}$F]-(I)

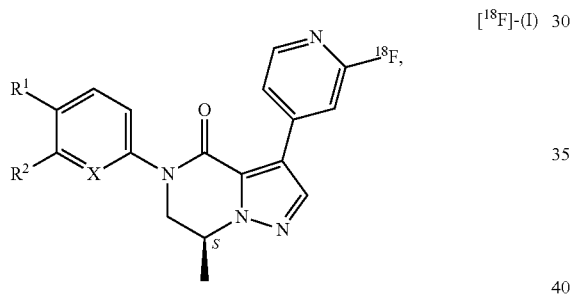

wherein

X, $R^1$ and $R^2$ are as defined herein, or a pharmaceutically acceptable salt or a solvate thereof.

In an additional embodiment of the present invention, the compound of Formula [$^{18}$F]-(I) is [$^{18}$F]-3

[$^{18}$F]-3

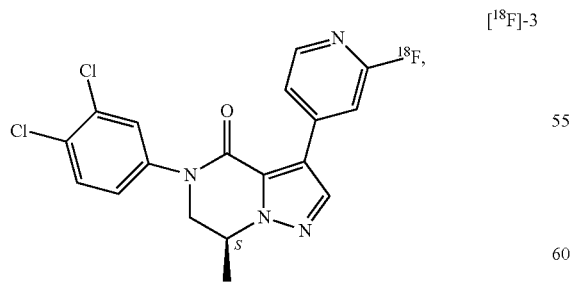

or a pharmaceutically acceptable salt or a solvate thereof.

In a further embodiment, the compound of Formula (I) as previously described is

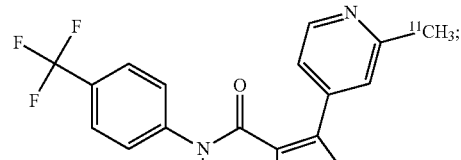

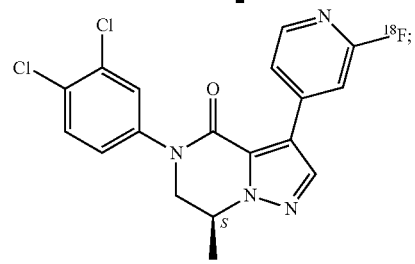

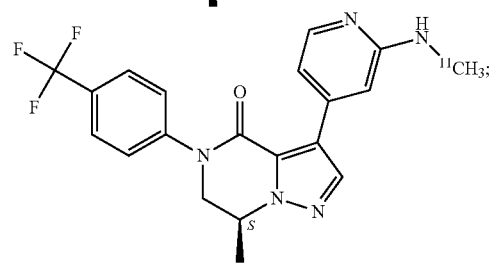

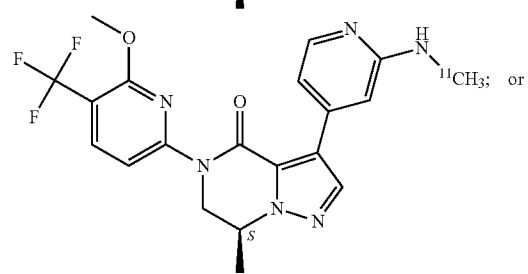

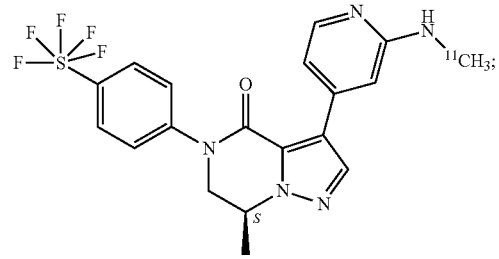

or a pharmaceutically acceptable salt or a solvate thereof.

As already mentioned, the compounds of Formula (I) and compositions comprising the compounds of Formula (I) can be used for imaging a tissue, cells or a mammal, in vitro or in vivo. In particular, the invention relates to a method of imaging or quantifying the mGluR2 receptor in a tissue, cells or a mammal in vitro or in vivo.

The cells and tissues are preferably central nervous system cells and tissues in which the mGluR2 receptors are abundant. As already mentioned, the mGluR2 receptor is abundant in central nervous system tissue, more in particular, in central nervous system tissue forming the brain; more in particular, forming the cerebral cortex, thalamic regions, accessory olfactory bulb, hippocampus, amygdala, caudate-putamen and nucleus accumbens.

When the method is performed in vivo, the compound of Formula (I) can be administered intravenously, for example, by injection with a syringe or by means of a peripheral intravenous line, such as a short catheter.

When the mammal is a human, the compound of Formula (I) or a sterile solution comprising a compound of Formula (I), may in particular be administered by intravenous administration in the arm, into any identifiable vein, in particular in the back of the hand, or in the median cubital vein at the elbow.

Thus, in a particular embodiment, the invention relates to a method of imaging a tissue or cells in a mammal, comprising the intravenous administration of a compound of Formula (I), as defined herein, or a composition comprising a compound of Formula (I) to the mammal, and imaging the tissue or cells with a positron-emission tomography imaging system.

Thus, in a further particular embodiment, the invention relates to a method of imaging a tissue or cells in a human, comprising the intravenous administration of a compound of Formula (I), as defined herein, or a sterile formulation comprising a compound of Formula (I) to the human, and imaging the tissue or cells with a positron-emission tomography imaging system.

In a further embodiment, the invention relates to a method of imaging or quantifying the mGluR2 receptor in a mammal, comprising the intravenous administration of a compound of Formula (I), or a composition comprising a compound of Formula (I) to the mammal, and imaging with a positron-emission tomography imaging system.

In another embodiment, the invention relates to the use of a compound of Formula (I) for imaging a tissue, cells or a mammal, in vitro or in vivo, or the invention relates to a compound of Formula (I), for use in imaging a tissue, cells or a mammal in vitro or in vivo, using positron-emission tomography.

The invention also relates to a method for imaging or quantifying the mGlu2 receptor in a mammal, the method comprising providing a detectable amount of a compound of Formula (I) to a mammal and detecting the compound of Formula (I) associated with mGlu2 receptor. The method also allows for determining mGlu2 receptor occupancy by other non-radiolabelled compounds, therefore, the invention relates to the compound of Formula (I) as defined herein, or the pharmaceutical composition according to the invention, for use in determining mGlu2 receptor site occupancy by other non-radiolabelled compounds.

Furthermore, the invention relates to a method of assessing a disorder or predisposition thereto related to the mGlu2 receptor in a subject, the method comprising providing a detectable amount of a compound of Formula (I) or pharmaceutical composition according to the invention, wherein the compound of Formula (I) passes the blood-brain barrier and preferentially binds to mGlu2 receptor in brain tissue, allowing the compound to distribute into the brain tissue, and imaging the brain tissue.

The compound is provided to a subject in a detectable amount and after sufficient time has passed for the compound to become associated with the mGlu2 receptor, the labelled compound is detected noninvasively.

As already mentioned hereinabove, the invention also encompasses novel compounds corresponding to the [$^{12}$C]-compounds or the [$^{19}$F]-compounds of Formula (I) and the pharmaceutically acceptable salts and solvates thereof. Said compounds have been found to display mGluR2 NAM activity. Therefore, the invention further relates to a pharmaceutical composition comprising a therapeutically effective amount of a novel [$^{12}$C]-compound or [$^{19}$F]-compound of Formula (I) or a pharmaceutically acceptable salt or a solvate thereof, and a pharmaceutically acceptable carrier or excipient.

Hence, the present invention also relates to a novel [$^{12}$C]-compound or [$^{19}$F]-compound of Formula (I) compound according to the general Formula (I), or a pharmaceutically acceptable salt or a solvate thereof, for use as a medicament.

The invention also relates to the use of a novel [$^{12}$C]-compound or [$^{19}$F]-compound of Formula (I), or a pharmaceutically acceptable salt or a solvate thereof, for the manufacture of a medicament.

Furthermore, the invention also relates to said novel [$^{12}$C]-compounds or [$^{19}$F]-compounds of Formula (I) and the pharmaceutically acceptable salts and the solvates thereof, for use as a medicament, and to said novel [$^{12}$C]-compounds or [$^{19}$F]-compounds of Formula (I) and the pharmaceutically acceptable salts and the solvates thereof, for use in the treatment or in the prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The invention also relates to the use of said novel [$^{12}$C]-compounds or [$^{19}$F]-compounds of Formula (I) and the pharmaceutically acceptable salts and the solvates thereof, in combination with an additional pharmaceutical agent for use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

Furthermore, the invention relates to a process for preparing a pharmaceutical composition according to the invention, characterized in that a pharmaceutically acceptable carrier is intimately mixed with a therapeutically effective amount of a said novel [$^{12}$C]-compound or [$^{19}$F]-compound of Formula (I), or a pharmaceutically acceptable salt or a solvate thereof.

The invention also relates to a method of treating or preventing a central nervous system disorder selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder comprising administering to a subject in need thereof, a therapeutically effective amount of a said novel [$^{12}$C]-compound or [$^{19}$F]-compound of Formula (I) or a pharmaceutically acceptable salt or a solvate thereof, or a therapeutically effective amount of a pharmaceutical composition according to the invention.

The invention also relates to a product comprising a novel [$^{12}$C]-compound or [$^{19}$F]-compound of Formula (I) or a pharmaceutically acceptable salt or a solvate thereof, and an additional pharmaceutical agent, as a combined preparation for simultaneous, separate or sequential use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

Definitions

As used herein, the term "composition" is intended to encompass a product comprising the specified ingredients in the specified amounts, as well as any product which results, directly or indirectly, from combinations of the specified ingredients in the specified amounts.

The term "detectable amount" refers to the concentration of compound above the lowest limit of detection of the imaging instrument, in particular, of the PET scanning instrument.

The absolute configuration is specified according to the Cahn-Ingold-Prelog system.

Addition salts of the compounds according to the invention also intended to be encompassed within the scope of this invention.

Acceptable salts of the compounds of the invention are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention. The pharmaceutically acceptable salts are defined to comprise the therapeutically active non-toxic acid addition salt forms that the compounds according to the invention are able to form. Said salts can be obtained by treating the base form of the compounds according to the invention with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzensulfonic acid, p-toluenesulfonic acid, cyclamic acid, salicylic acid, p-aminosalicylic acid and pamoic acid.

Conversely, said salt forms can be converted into the free base form by treatment with an appropriate base.

In addition, some of the compounds of the present invention may form solvates with water (i.e., hydrates) or common organic solvents, and such solvates are also intended to be encompassed within the scope of this invention.

The term "subject" as used herein, refers to an animal, preferably a mammal, most preferably a human, who is or has been the object of treatment, observation or experiment. Unless otherwise stated, "subject" includes both, healthy animals and animals afflicted by different diseases or disorders.

The term "mammal" refers, in particular to humans, mice, dogs and rats.

The term "cell" refers to a cell expressing or incorporating the mGlu2 receptor.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006).

PREPARATION

The compounds according to the invention can generally be prepared by a succession of steps, each of which is known to the skilled person. In particular, the compounds can be prepared according to the following synthesis methods.

A. Preparation of the Final Compounds

Compounds of Formula (I) in their non-radiolabeled version herein referred to as [$^{12}$C]-(I) or [$^{19}$F]-(I) can be prepared by synthesis methods well known to the person skilled in the art, for example:

Experimental Procedure 1

Final compounds according to Formula [$^{12}$C]/[$^{19}$F]-(I) can be prepared by a Goldberg coupling reaction of a compound of Formula (II) with an appropriate (hetero)aryl halide of Formula (III) where halo$^1$ is in particular bromo or iodo, according to conditions known to the skilled person. Such conditions include for example using a suitable copper (I) catalyst such as copper(I) iodide, in the presence of a ligand, such as N,N'-dimethylethylenediamine, in the presence of a base, such as inorganic carbonates, for example sodium carbonate ($Na_2CO_3$) or potassium carbonate ($K_2CO_3$), in a suitable solvent, such as toluene or a mixture of toluene and DMF, under suitable reaction conditions, such as at a convenient temperature, typically ranging between 100° C. and 140° C., in particular 110° C., for a period of time to ensure the completion of the reaction. A compound of Formula (III) can be obtained commercially or made according to procedures known in the art. In Reaction Scheme 1, X, $R^1$, $R^2$ and $R^3$ are as defined hereinabove.

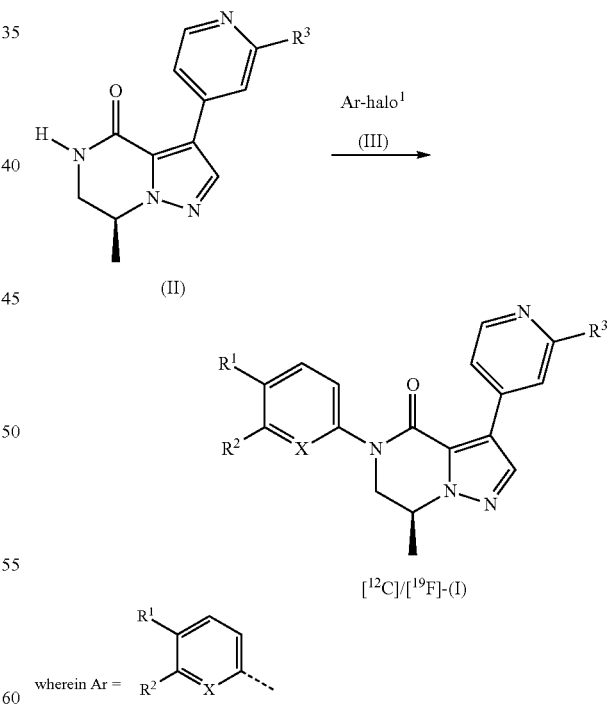

Experimental Procedure 2

Alternatively, final compounds according to Formula [$^{12}$C]/[$^{19}$F]-(I) can be prepared by a Suzuki type coupling reaction of a compound of Formula (IVa) with a suitable boron species or a compound of Formula (IVb), wherein $R^4$ and $R^5$ may be each independently selected from H, $C_{1-4}$alkyl or $R^4$ and $R^5$ are taken together to form for example a bivalent radical of formula —$CH_2CH_2$—, —$CH_2CH_2CH_2$— or —$C(CH_3)_2C(CH_3)_2$—, with a suitable 4-pyridinyl halide derivative in the presence of a palladium catalyst, according to reaction conditions known to the skilled person. Such reaction conditions include the use of a palladium catalyst, such as tetrakis(triphenylphosphine)palladium(0) or an alternative catalyst system prepared in situ from $Pd(OAc)_2$ and $PPh_3$, a suitable base, such as $Na_2CO_3$, $K_2CO_3$, NaOAc, $NaHCO_3$ or $K_3PO_4$, and in a suitable solvent, such as 1,4-dioxane, or a mixture of DME and water. Degassing the reaction mixture with an inert gas, such as $N_2$ or argon, and heating the reaction mixture to high temperatures, such as reflux temperature under classical heating or microwave irradiation, in particular 80° C., may enhance the reaction outcome. In Reaction Schemes 2a and 2b, X, $R^1$, $R^2$ and $R^3$ are as defined hereinabove.

Reaction Scheme 2a

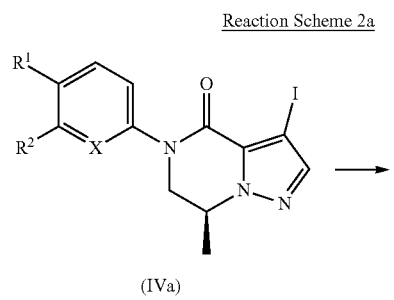

(IVa)

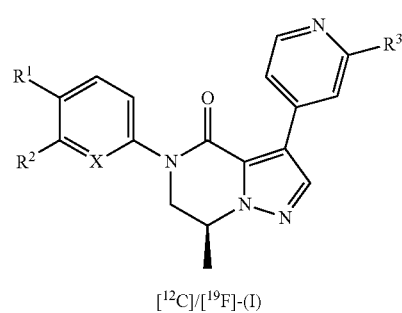

[$^{12}$C]/[$^{19}$F]-(I)

Reaction Scheme 2b

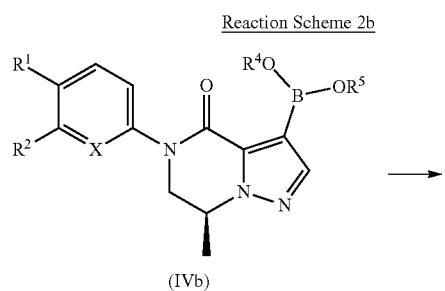

(IVb)

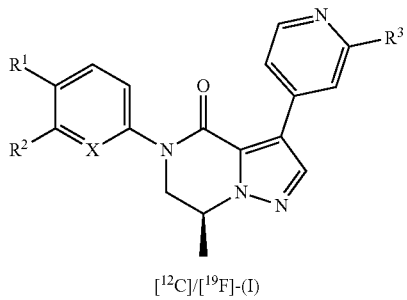

[$^{12}$C]/[$^{19}$F]-(I)

The suitable boron species may be selected for example from a boronic acid or a boronate ester, which may be conveniently represented as a compound of Formula (IIIa),

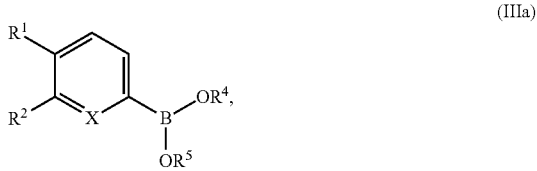

(IIIa)

wherein $R^4$ and $R^5$ may be each independently selected from H, $C_{1-4}$alkyl or $R^4$ and $R^5$ are taken together to form for example a bivalent radical of formula —$CH_2CH_2$—, —$CH_2CH_2CH_2$— or —$C(CH_3)_2C(CH_3)_2$— and X, $R^1$, and $R^2$ are as defined hereinabove. A skilled person can envisage that the reaction under Reaction Scheme 2a can also be performed under similar conditions, when the compound of Formula (IVa) bears a bromo group in place of an iodo group. Such a reaction can be represented as in Reaction Scheme 2c, wherein the compound of Formula (IV), wherein halo is, in particular bromo or iodo and X, $R^1$, $R^2$ and $R^3$ are as defined hereinabove, undergoes a Suzuki type coupling as described hereinbefore.

Reaction Scheme 2c

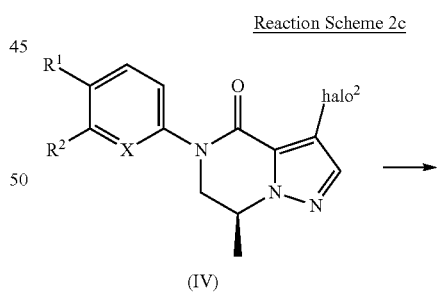

(IV)

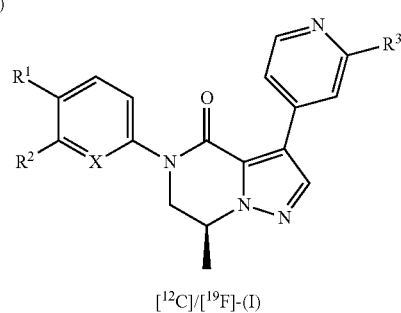

[$^{12}$C]/[$^{19}$F]-(I)

Experimental Procedure 3

Alternatively, final compounds according to Formula [$^{12}$C]/[$^{19}$F]-(I) can be prepared in one pot starting from a compound of Formula (II). First, a reaction of nucleophilic substitution of a compound of Formula (II) with an appropriate (hetero)aryl halide of Formula (III), as defined hereinbefore, in the presence of a base such as for example sodium hydride in a suitable solvent such as for example DMF, followed by an intramolecular peptide type coupling of compound of Formula (V) applying typical peptide type coupling conditions. Typically, peptide coupling conditions can be applied, such as stirring the starting materials, dissolved in a suitable solvent, such as DMF, in the presence of a peptide coupling agent, such as HATU and in the presence of a base, such as TEA. In Reaction Scheme 3, X, $R^1$, $R^2$ and $R^3$ are as defined hereinabove.

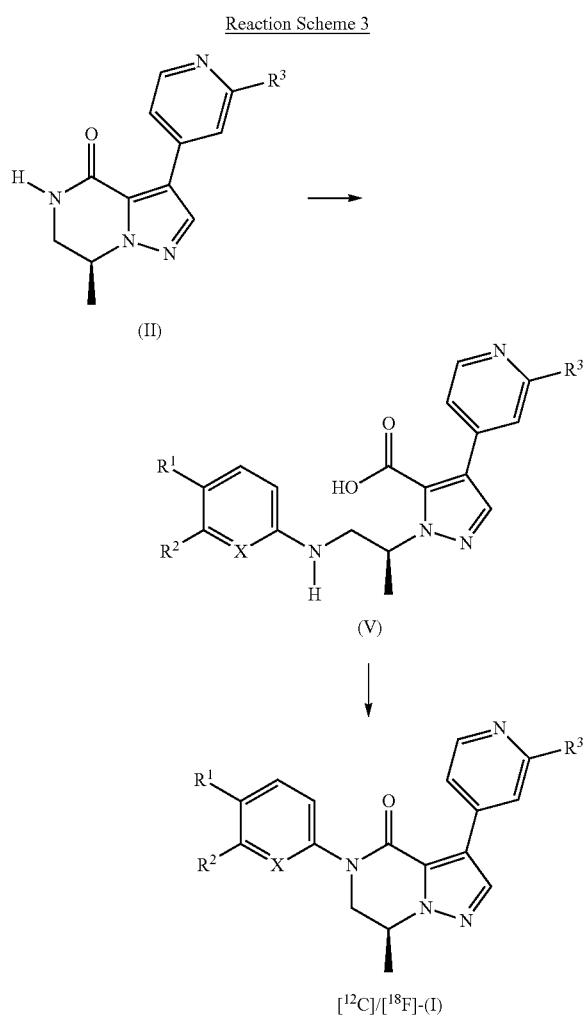

Reaction Scheme 3

[$^{12}$C]/[$^{18}$F]-(I)

Alternatively, final compounds according to Formula [$^{12}$C]/[$^{19}$F]-(I) can be prepared in one pot starting from a compound of Formula (II). First by a coupling reaction of a compound of Formula (II) with an appropriate (hetero)aryl halide of Formula (III) in the presence of a palladium catalyst, such as tetrakis(triphenylphosphine)palladium(0), in the presence of a ligand, such as 4,5-bis(diphenylphosphino)-9,9-dimethylxanthene, in the presence of a base, such as $Cs_2CO_3$ and in a suitable solvent, such as 1,4-dioxane, under suitable reaction conditions, such as at a convenient temperature, typically ranging between 100° C. and 140° C., for a period of time to ensure the completion of the reaction, followed by an intramolecular peptide type coupling of compound of Formula (V) applying typical peptide type coupling conditions. Typically, peptide coupling conditions can be applied, such as stirring the starting materials, dissolved in a suitable solvent, such as DMF, in the presence of a peptide coupling agent, such as HATU and in the presence of a base, such as TEA. In Reaction Scheme 3, X, $R^1$, $R^2$ and $R^3$ are as defined hereinabove.

B. Preparation of the Intermediate Compounds

Experimental Procedure 4

Intermediate compounds according to Formula (II) (Reaction Scheme 4a) can be prepared following art known procedures, such as by subjecting an intermediate compound of Formula (VIa) to a Suzuki type coupling reaction under conditions known to a skilled person. Such conditions include for example, reacting the intermediate compound of Formula (VIa) with a suitable boron species, such as for example a boronic acid or a boronate ester, for example as described in Experimental procedure 2 hereinbefore, in the presence of a palladium catalyst, such as tetrakis(triphenylphosphine)palladium(0) or an alternative catalyst system prepared in situ from $Pd(OAc)_2$ and $PPh_3$, a suitable base, such as $Na_2CO_3$, $K_2CO_3$, $NaHCO_3$ and $K_3PO_4$, and in a suitable solvent, such as 1,4-dioxane, or a mixture of DME and water. Degassing the reaction mixture with an inert gas, such as $N_2$ or argon, and heating the reaction mixture to high temperatures, such as reflux temperature, in particular 80° C., may enhance the reaction outcome. In Reaction Scheme 4a, $R^3$ is as defined hereinabove.

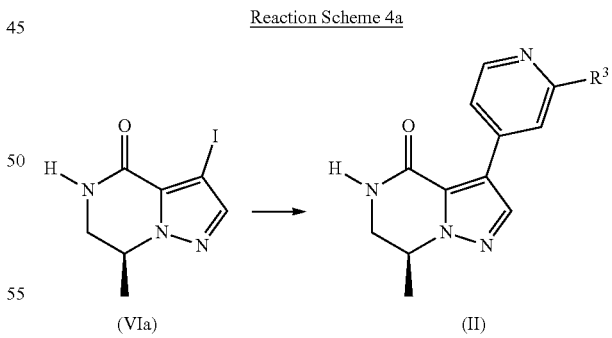

Reaction Scheme 4a

A skilled person can envisage that the reaction under Reaction Scheme 4a can also be performed under similar conditions, when the compound of Formula (VIa) bears a bromo group in place of a iodo group. Such a reaction can be represented as in Reaction Scheme 4b, wherein the compound of Formula (VI), wherein halo$^2$ is, in particular bromo or iodo and all other variables are as defined in Formula (I), undergoes a Suzuki type coupling as described hereinbefore.

Reaction Scheme 4b

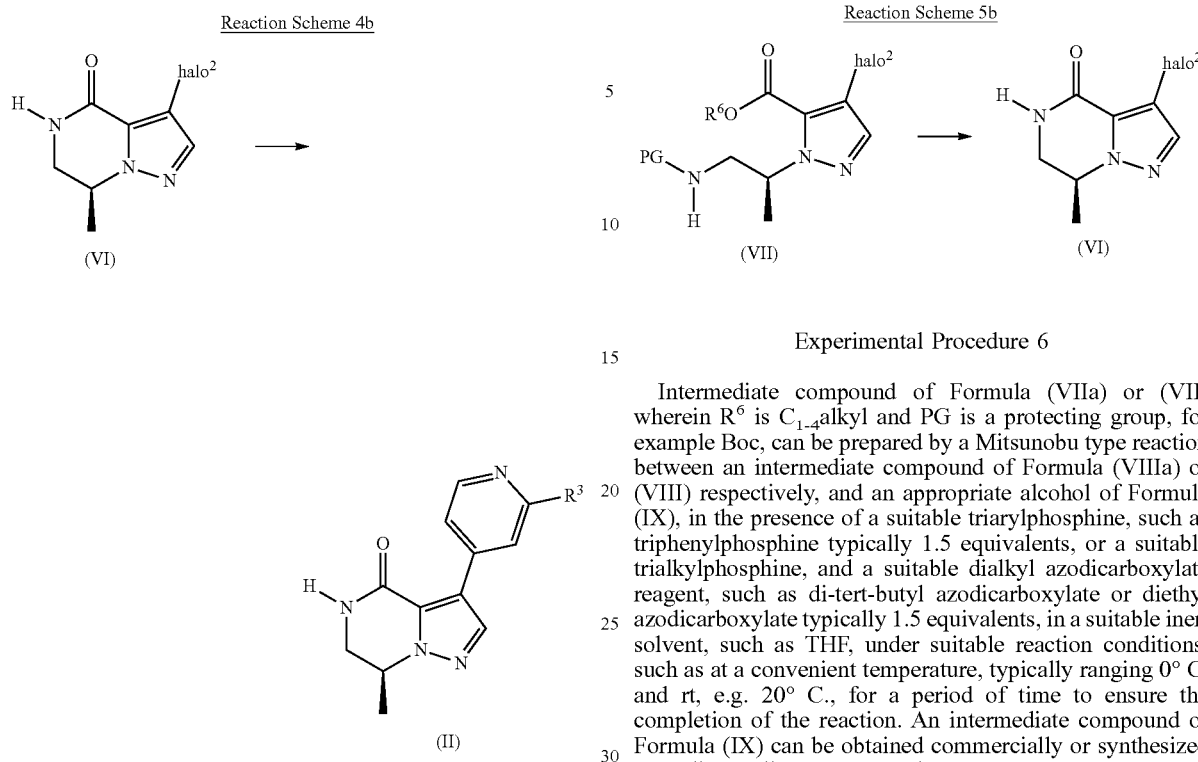

(VI)

(II)

Reaction Scheme 5b (VII) → (VI)

Experimental Procedure 6

Intermediate compound of Formula (VIIa) or (VII) wherein $R^6$ is $C_{1-4}$alkyl and PG is a protecting group, for example Boc, can be prepared by a Mitsunobu type reaction between an intermediate compound of Formula (VIIIa) or (VIII) respectively, and an appropriate alcohol of Formula (IX), in the presence of a suitable triarylphosphine, such as triphenylphosphine typically 1.5 equivalents, or a suitable trialkylphosphine, and a suitable dialkyl azodicarboxylate reagent, such as di-tert-butyl azodicarboxylate or diethyl azodicarboxylate typically 1.5 equivalents, in a suitable inert solvent, such as THF, under suitable reaction conditions, such as at a convenient temperature, typically ranging 0° C. and rt, e.g. 20° C., for a period of time to ensure the completion of the reaction. An intermediate compound of Formula (IX) can be obtained commercially or synthesized according to literature procedures.

Intermediate compound of Formula (VIIIa) wherein $R^6$ is $C_{1-4}$alkyl, can be prepared via a reaction of halogenation of intermediate of Formula (X) with a halogenating reagent such as N-iodosuccinimide, in an inert solvent such as dichloromethane, under suitable reaction conditions, such as at a convenient temperature, typically rt, for a period of time to ensure the completion of the reaction. Intermediate compound of Formula (VIII), wherein $R^6$ is methyl and halo is bromo, can be obtained commercially and is a particularly preferred material for use in the synthesis, including large scale, of a variety of final compounds of Formula $[^{12}C]$/$[^{19}F]$-(I) according to the general procedures described herein. An intermediate compound of Formula (X) can be obtained commercially or synthesized according to literature procedures.

In Reaction Scheme 6a and 6b, $halo^2$ is, in particular bromo or iodo, $R^6$ is $C_{1-4}$alkyl, PG is a protecting group, such as for example Boc.

Experimental Procedure 5

Intermediate compound of Formula (VIa) or of Formula (VI) can be prepared by removal of the protecting group, for example a Boc group, in an intermediate of Formula (VIIa) or of Formula (VII), respectively, for example in the presence of acidic media, such as hydrochloric acid, in an inert solvent such as 1,4-dioxane or acetonitrile or EtOAc, under suitable reaction conditions, such as at a convenient temperature, such as from 15 to 80° C., typically 80° C. or from 15-30° C. depending on the solvent system, for a period of time to ensure the completion of the reaction followed by treatment with a base such as $Na_2CO_3$, $K_2CO_3$ or $NaHCO_3$, under suitable reaction conditions, such as at a convenient temperature, typically ranging between 0° C. and 40° C., in particular from 15 to 30° C., for a period of time to ensure the completion of the reaction. In Reaction Schemes 5a and 5b, $halo^2$ is, in particular bromo or iodo, $R^6$ is $C_{1-4}$alkyl, PG is a protecting group, for example Boc.

Reaction Scheme 5a (VIIa) → (VIa)

Reaction Scheme 6a

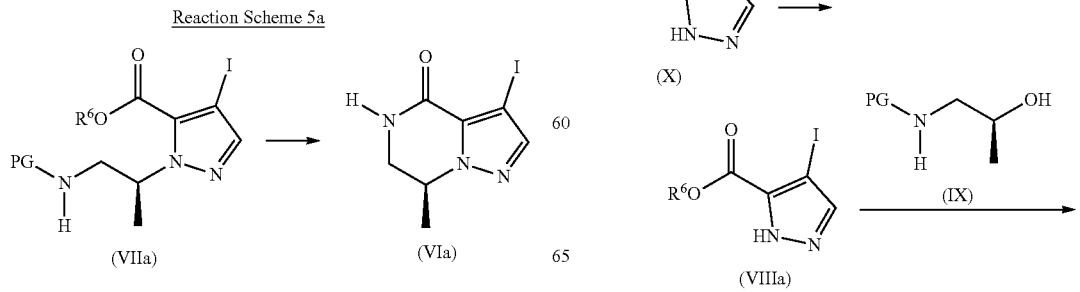

(X)

(VIIIa)  (IX)

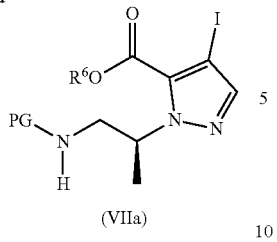

(VIIa)

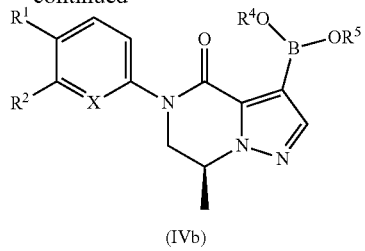

(IVb)

Reaction Scheme 6b

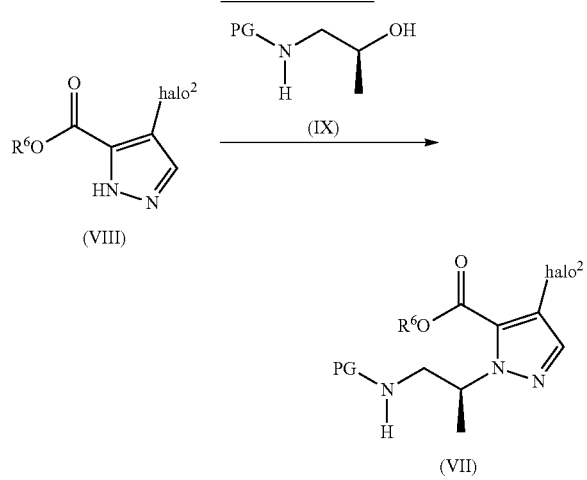

(VII)

Experimental Procedure 7

Intermediate compound of Formula (IVb) can be prepared via a reaction of boronic ester or boronic acid formation starting from an intermediate of Formula (IVa) with a trans metallating agent such as for example BuLi or a Grignard reagent, a particular example of reagents includes isopropylmagnesium chloride lithium chloride complex solution and a boron species such as 2-isopropoxy-4,4,5,5-tetramethyl-1,3,2-dioxaborolane, in an inert solvent such as anhydrous THF, under suitable reaction conditions, such as at a convenient temperature, typically −25° C., for a period of time to ensure the completion of the reaction. Depending on reaction conditions, boronic ester or boronic acid are obtained. In Reaction Scheme 7, $R^4$ and $R^5$ are H or $C_{1-4}$ alkyl or $R^4$ and $R^5$ are taken together to form for example a bivalent radical of formula —$CH_2CH_2$—, —$CH_2CH_2CH_2$— or —$C(CH_3)_2C(CH_3)_2$—, and X, $R^1$ and $R^2$ are as defined hereinabove.

Reaction Scheme 7

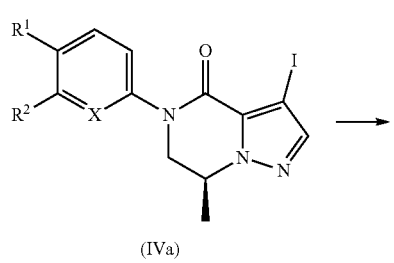

(IVa)

Experimental Procedure 8

Intermediate compound of Formula (IVa) can be prepared via a reaction of halogenation of an intermediate of Formula (XI) with a halogenating reagent such as iodine, in the presence of ammonium cerium(IV) nitrate and in an inert solvent such as acetonitrile, under suitable reaction conditions, such as at a convenient temperature, typically 70° C., for a period of time to ensure the completion of the reaction. In an analogous manner, intermediate compound of Formula (VIa) can be prepared from intermediate of Formula (XII). In Reaction Schemes 8a and 8b, X, $R^1$ and $R^2$ are as defined hereinabove.

Reaction Scheme 8a

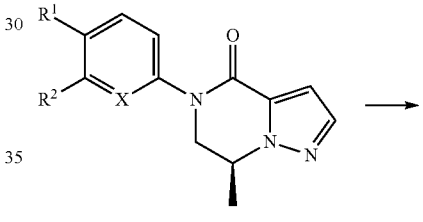

(XI)

(IVa)

Reaction Scheme 8b

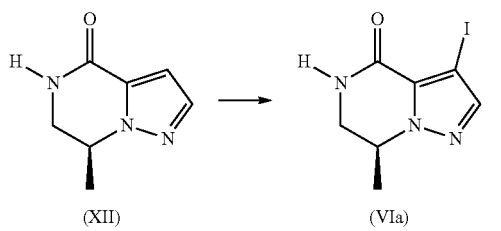

(XII) (VIa)

Experimental Procedure 9

Intermediate compound of Formula (XI) can be prepared by a coupling reaction of an intermediate compound of Formula (XII) with an appropriate (hetero)aryl halide of Formula (III) as defined hereinbefore with a suitable copper (I) catalyst such as copper(I) iodide, in the presence of a ligand, such as N,N'-dimethylethylenediamine, in the presence of a base, such as $Na_2CO_3$, in a suitable solvent, such as toluene, under suitable reaction conditions, such as at a convenient temperature, typically ranging between 100° C. and 140° C., for a period of time to ensure the completion of the reaction. In an analogous manner, intermediate compound of Formula (IV) can be prepared from intermediate of Formula (VI). An intermediate compound of Formula (III) can be obtained commercially. In Reaction Schemes 9a and 9b, X, $R^1$ and $R^2$ are as defined hereinabove and $halo^2$ is, in particular bromo or iodo.

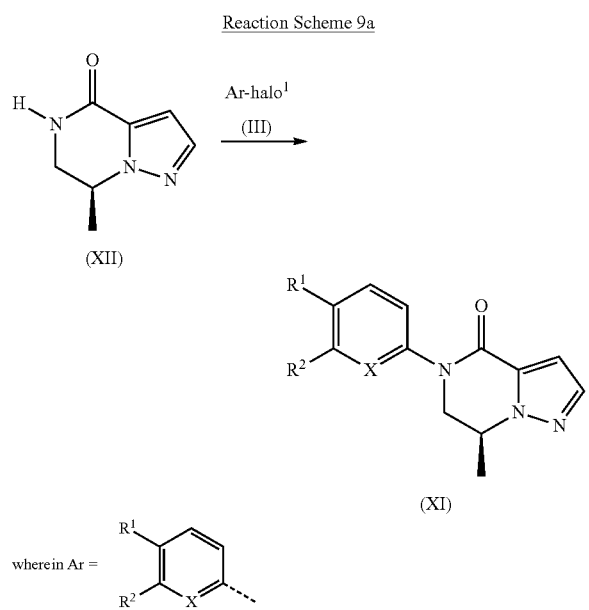

Formula (XIII), for example in the presence of acidic media, such as hydrochloric acid, in an inert solvent such as 1,4-dioxane, under suitable reaction conditions, such as at a convenient temperature, typically 80° C., for a period of time to ensure the completion of the reaction followed by treatment with a base, such as $Na_2CO_3$ or $NaHCO_3$, under suitable reaction conditions, such as at a convenient temperature, typically ranging between 0° C. and 40° C., for a period of time to ensure the completion of the reaction. In Reaction Scheme 10, $R^6$ is $C_{1-4}$alkyl, PG is a protecting group.

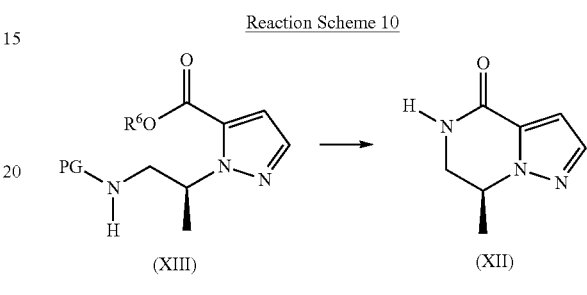

Experimental Procedure 11

Intermediate compound of Formula (XIII) wherein $R^6$ is $C_{1-4}$alkyl and PG is a protecting group, can be prepared by a Mitsunobu type reaction between a compound of Formula (XIV) and an appropriate alcohol of Formula (IX), in the presence of a suitable triarylphosphine, such as triphenylphosphine, or a suitable trialkylphosphine, and a suitable dialkyl azodicarboxylate reagent, such as di-tert-butyl azodicarboxylate, in a suitable inert solvent, such as THF, under suitable reaction conditions, such as at a convenient temperature, typically rt, for a period of time to ensure the completion of the reaction. Intermediate compounds of Formula (XIV) and of Formula (IX) can be obtained commercially or synthesized according to literature procedures. In Reaction Scheme 11, $R^6$ is $C_{1-4}$alkyl, PG is a protecting group.

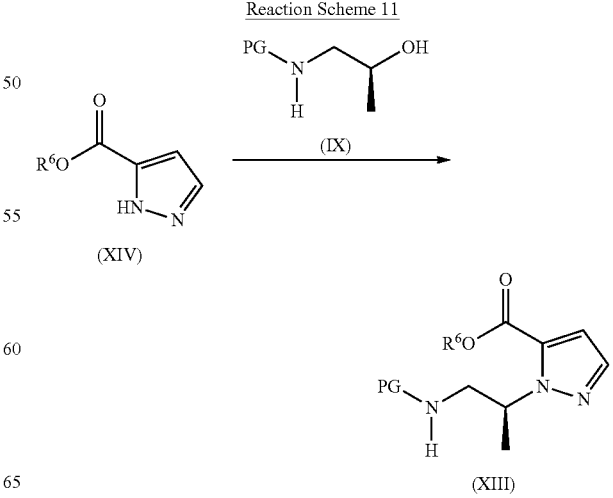

Experimental Procedure 10

Intermediate compound of Formula (XII) can be prepared by removal of the protecting group in an intermediate of

Experimental Procedure 12

Intermediate compound of Formula (XIV) wherein $R^6$ is $C_{1-4}$alkyl can be obtained by esterification of the commercially available intermediate compound of Formula (XV), by methods known to the person skilled in the art, or may be commercially available. The reaction can be performed for example in the presence of an acidic agent, such as sulfuric acid, and an alcohol, such as EtOH, in a suitable solvent, such as EtOH, under suitable reaction conditions, such as at a convenient temperature, typically between 80° C. and 100° C., for a period of time to ensure the completion of the reaction. In Reaction Scheme 12, $R^6$ is $C_{1-4}$alkyl.

Reaction Scheme 12

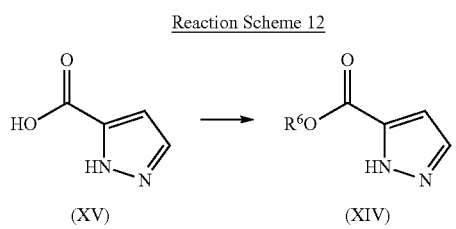

C. Preparation of the Radioligand Precursors

Experimental Procedure 13

A precursor compound of Formula (P-I) can be obtained by methylation of a compound of Formula (XVI) by reaction with a suitable alkylating reagent, such as $CH_3I$, in the presence of a suitable base, for example, $K_2CO_3$, and in a polar solvent, such as MeOH, under suitable reaction conditions, such as stirring at rt for several days. A compound of Formula (XVI) can be obtained from a compound of Formula (IVb) by reaction with a 4-halo-2-(dimethylamino)pyridine, such as 4-bromo-2-dimethylamino)pyridine under suitable reaction conditions, such as reaction in the presence of a base, e.g. KOH, in a suitable reaction inert solvent, such as THF. Flow reactor conditions can enhance the reaction outcome. In reaction Scheme 13, all variables are as described hereinabove.

Reaction Scheme 13

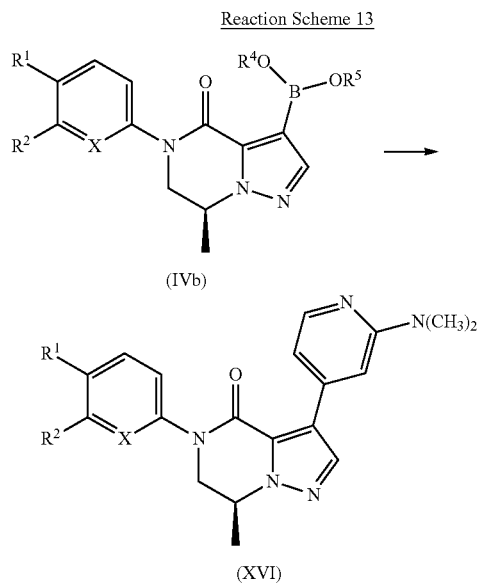

Experimental Procedure 14

A precursor compound of Formula (P-II) can be obtained by formation of an organotin reagent by reaction of a compound of Formula (XVII) with a suitable reagent, such as hexabutylditin in the presence of $Pd(PPh_3)_2Cl_2$ in a suitable solvent such as dioxane, under suitable reaction conditions, such as stirring at a moderate temperature for several minutes. A compound of Formula (XVII) can be obtained from the corresponding chloride compound of Formula (XVIII) by a transhalogenation reaction with sodium iodide in the presence of acetyl chloride. A compound of Formula (XVIII) can be obtained by reaction of a compound of Formula (IVa) according to the reaction conditions such as those described in experimental procedure 2. In Reaction Scheme 14, all variables are as described hereinabove.

Reaction Scheme 14

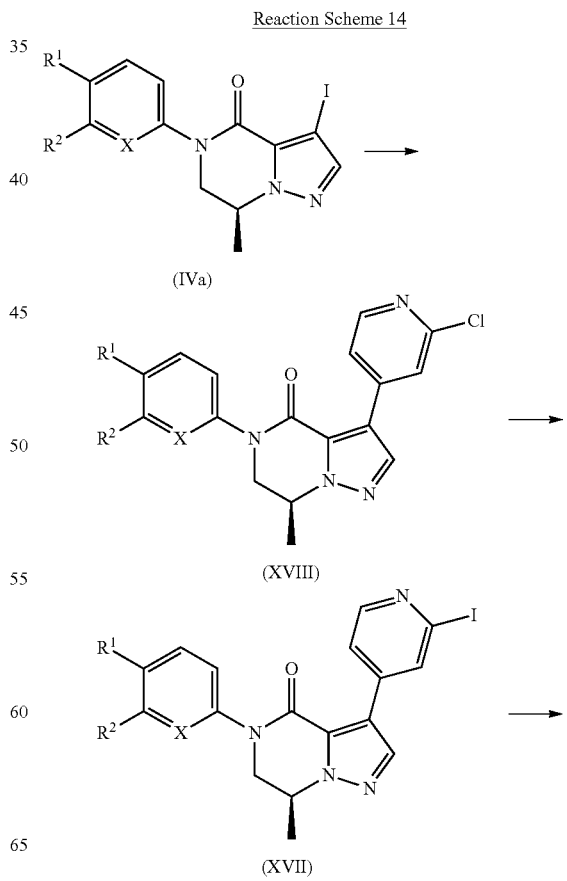

27

-continued

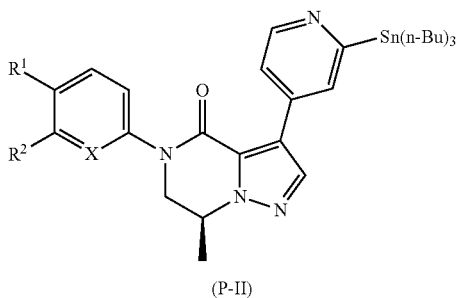

(P-II)

Experimental Procedure 15

A precursor compound of Formula (P-III) can be obtained by protection of the amine functionality in a compound of Formula (IXX), under reaction conditions known to the skilled person, typically by reaction of (IXX) with di-tert-butyl dicarbonate in a polar solvent, such as tBuOH at room temperature for a period of time required to complete the reaction. A compound of Formula (IXX) can be synthesized from a compound of formula (IVa) according to reaction conditions such as those described in experimental procedure 2. In Reaction Scheme 15, all variables are as described hereinabove.

Reaction Scheme 15

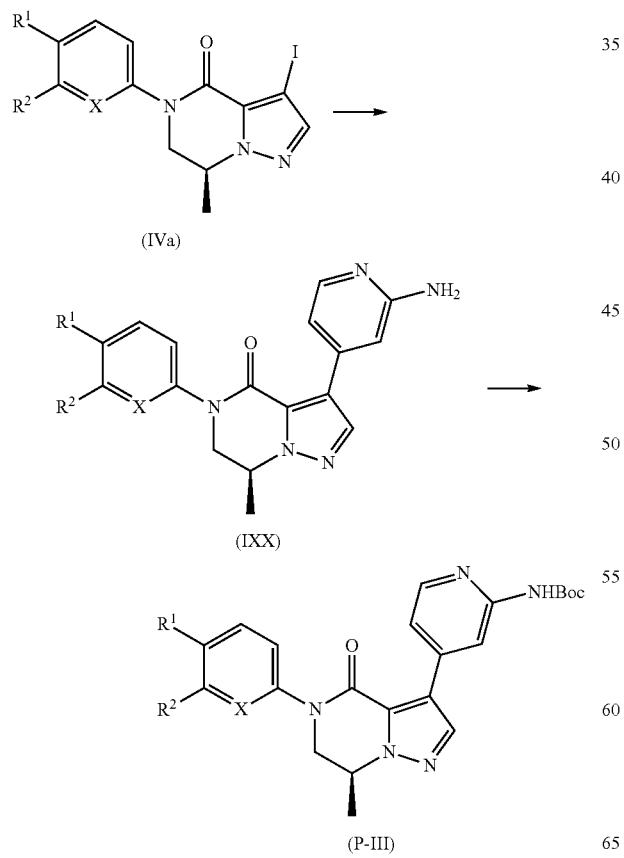

28

Preparation of the Radioligands

Experimental Procedure 16

$[^{11}C]$-Radiolabelled compounds of Formula (I) wherein $R^3$ is $-NH[^{11}C]CH_3$ and the rest of variables are as defined in Formula (I), herein referred to as compounds of Formula $[^{11}C]$-(I-a), can be synthesized in two steps by heating their corresponding N-Boc protected precursor (P-III) with a suitable reagent, such as $[^{11}C]$MeI under appropriate conditions, typically in a solvent such as anhydrous DMF in the presence of a base, such as NaH for a period of time to allow completion of the reaction, for example, 4 min, at an appropriate temperature, typically 80° C., to yield (XX). Boc cleavage from (XX) can be accomplished using conditions known to the skilled person, such as stirring in acidic medium under heat, such as for example, at 100° C. with HCl in dioxane. In Reaction Scheme 16, all variables are as described in Formula (I).

Reaction Scheme 16

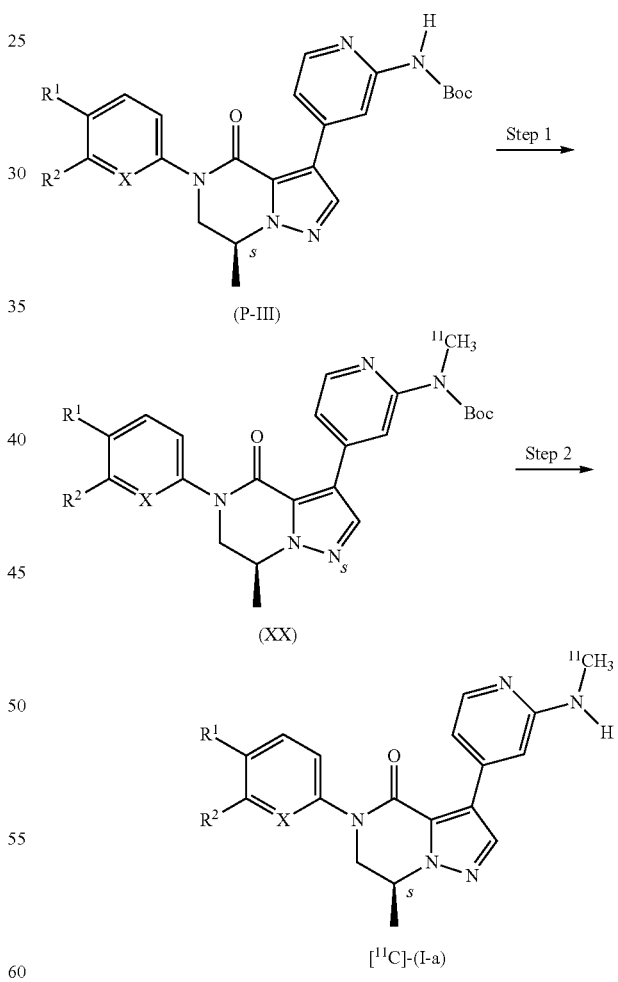

Experimental Procedure 17

Compounds of Formula (I) wherein $R^3$ is $[^{11}C]CH_3$, herein referred to as compounds of Formula $[^{11}C]$-(I-b), can be synthesized using a Stille coupling reaction. Typically, the reaction is performed with an appropriate tributyl stannyl precursor (P-II) wherein all variables are as defined hereinbefore, and [$^{11}$C]CH$_3$I in the presence of a palladium-catalyst, such as Pd(PPh$_3$)$_4$ under appropriate conditions, typically at 100° C. in anhydrous DMF.

Reaction Scheme 17

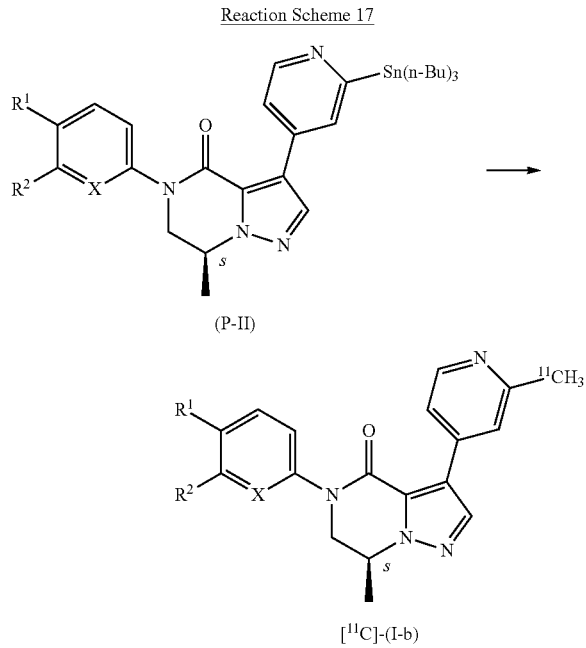

Experimental Procedure 18

Compounds of Formula (I) wherein R$^3$ is [$^{18}$F], herein referred to as a compound of formula [$^{18}$F]-(I), can be synthesized by heating the corresponding trimethyl ammonium precursor (P-I), wherein all variables are as described hereinbefore, at 82° C. in anhydrous CH$_3$CN with $^{18}$F$^-$/4,7,13,16,21,24-hexaoxa-1,10-diazabicyclo[8.8.8]hexacosane (commercialized under the tradename Kryptofix®2.2.2) in the presence of K$_2$C$_2$O$_4$ as base. The skilled person will also envisage the possibility of replacing K$_2$C$_2$O$_4$ with KHCO$_3$ and using a different leaving group in the precursor. Demethylation of the trimethyl ammonium precursor was typically observed as a side reaction.

Reaction Scheme 18

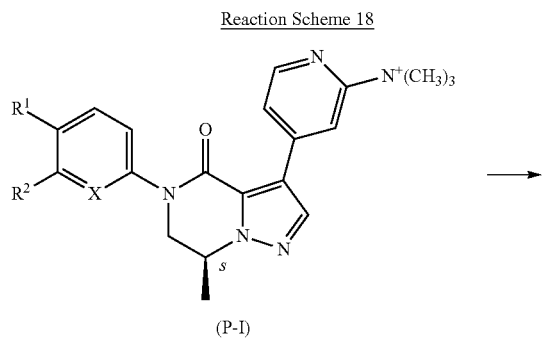

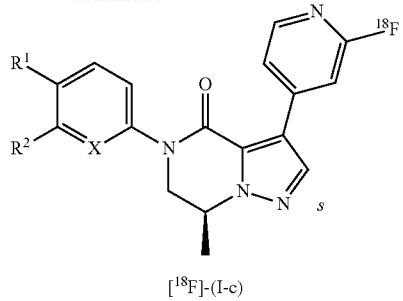

[$^{18}$F]-(I-c)

The crude reaction mixtures were then purified using semi-preparative HPLC.

Applications

The compounds according to the present invention find various applications for imaging tissues, cells or a mammal, both in vitro and in vivo. Thus, for instance, they can be used to map the differential distribution of mGluR2 in subjects of different age and sex. Further, they allow one to explore for differential distribution of mGluR2 in subjects afflicted by different diseases or disorders. Thus, abnormal distribution may be helpful in diagnosis, case finding, stratification of subject populations, and in monitoring disease progression in individual subjects. The radioligands may further find utility in determining mGluR2 site occupancy by other ligands. Since the radioligand is administered in trace amounts, i.e. in detectable amounts for example for PET imaging, no therapeutic effect may be attributed to the administration of the radioligands according to the invention.

Experimental Part

I. Chemistry

As used herein, the term "aq." means aqueous, "BEH" bridged ethylsiloxane/silica hybrid, "Boc"/"BOC" means tert-butoxycarbonyl, "tBuOH" means tert-butanol, "DAD" Diode Array Detector, "DCE" means 1,2-dichloroethane, "DCM" means dichloromethane, "DIPE" means diisopropyl ether, "DME" means dimethyloxyethane, "DMF" means N,N-dimethylformamide, "DMSO" means dimethyl sulfoxide, "DSC" means differential scanning calorimetry, "Et$_3$N/TEA" means triethylamine, "EtOH" means ethanol, "EtOAc" means ethyl acetate, "h" means hours, "HATU" means 1-[Bis(dimethylamino)methylene]-1H-1,2,3-triazolo[4,5-b]pyridinium 3-oxid hexafluorophosphate, "HPLC" means high-performance liquid chromatography, "LCMS" means liquid chromatography/mass spectrometry, "IPA" means isopropyl alcohol, "LCT" means LC-Time of Flight, "MeOH" means methanol, "[M+H]$^+$" means the protonated mass of the free base of the compound, "[M−H]$^-$" means the deprotonated mass of the free base of the compound, "min" means minutes, "m.p." means melting point, "MSD" Mass Selective Detector, "MTBE" means methyl tert-butyl ether, "mw/MW" means microwave, "QTOF" Quadrupole-Time of Flight, "quant." means quantitative, "r.m." means reaction mixture, "RP" means reverse phase, "r.t./RT" means room temperature" "R$_t$" means retention time (in minutes), "sat." means saturated, "sol." means solution, "SQD" Single Quadrupole Detector, "THF" means tetrahydrofuran, "UV" means ultraviolet.

Microwave assisted reactions were performed in a single-mode reactor: Biotage Initiator™ Sixty microwave reactor (Biotage) or in a multimode reactor: MicroSYNTH Labstation (Milestone, Inc.).

Reactions under pressure were performed in a pressure tube (Q-Tube™) from Q-Labtech LLC.

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques. Automated flash column chromatography was performed using ready-to-connect cartridges from Merck, on irregular silica gel, particle size 15-40 μm (normal phase disposable flash columns) on an SPOT or LAFLASH system from Armen Instrument.

Nuclear Magnetic Resonance (NMR): For a number of compounds, ¹H NMR spectra were recorded either on a Bruker Avance III, on a Bruker DPX-400 or on a Bruker AV-500 spectrometer with standard pulse sequences, operating at 400 MHz and 500 MHz, respectively. Chemical shifts (δ) are reported in parts per million (ppm) downfield from tetramethylsilane (TMS), which was used as internal standard.

Several methods for preparing the compounds of this invention are illustrated in the following examples, which are intended to illustrate but not to limit the scope of the present invention. Unless otherwise noted, all starting materials were obtained from commercial suppliers and used without further purification.

A. Synthesis of Intermediates

Intermediate 1 (I-1)

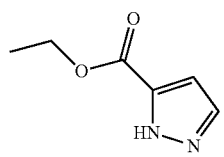

Sulfuric acid (10 mL, 187.6 mmol) was added to a solution of 1-H-pyrazole-3-carboxylic acid (1.93 g, 17.22 mmol) in EtOH (20 mL). The mixture was stirred at 90° C. for 15 h. Then it was allowed to cool to rt and the solvents were evaporated in vacuo. The residue was poured into water and the solution basified with K₂CO₃ and extracted with EtOAc. The organic layer was separated, dried (MgSO₄), filtered and the solvent evaporated in vacuo to yield intermediate compound I-1 as a white solid (2.28 g, 93% purity, 94%) which was used in the following step without further purification.

Intermediate 2 (I-2)

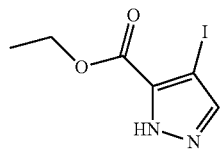

Intermediate I-1 (100 g, 0.68 mol), N-iodosuccinimide (213.5 g, 0.95 mol) were dissolved in DCM (2 L). The mixture was stirred at rt for 24 h. The mixture was treated with a sat. sol. of Na₂S₂O₃ and a sat. sol. of Na₂CO₃ and extracted with DCM. The organic layer was separated, dried (MgSO₄), filtered and the solvent evaporated in vacuo to yield intermediate compound I-2 as a white solid (160 g, 85%).

Intermediate 3 (I-3)

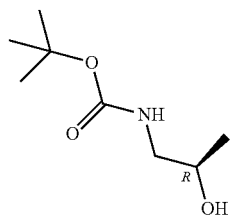

Di-tert-butyl dicarbonate (58.1 g, 266.3 mmol) in DCM (50 mL) was added to a stirred solution of (R)-(−)-1-amino-2-propanol in DCM (50 mL) at 0° C. under nitrogen. The mixture was stirred at rt for 2 h. The mixture was diluted with cooled water and extracted with DCM. The organic layer was separated, dried (Na₂SO₄), filtered and the solvents evaporated in vacuo to yield intermediate I-3 as a colorless oil (47 g, quant.). The product was used in the next step without further purification.

Intermediate 4 (I-4)

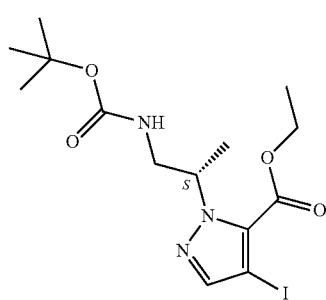

Di-tert-butyl azodicarboxylate (4.67 g, 20.3 mmol) was added to a stirred solution of intermediate I-2 (3 g, 11.28 mmol), intermediate I-3 (4.44 g, 22.55 mmol) and triphenylphosphine (5.32 g, 20.3 mmol) in THF (56 mL) under nitrogen. The mixture was stirred at rt for 5 h. The solvent was evaporated in vacuo and the crude product was triturated with DIPE. The solid was filtered and the filtrate was evaporated in vacuo. The crude product was purified by flash column chromatography (silica; EtOAc in Heptane 0/100 to 30/70). The desired fractions were collected and the solvents evaporated in vacuo to give intermediate compound I-4 as a colorless oil (4.9 g, 91% purity, 93%).

Intermediate 5 (I-5)

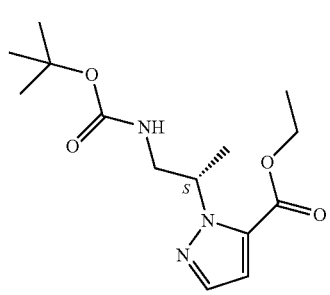

Intermediate compound I-5 was synthesized following a similar approach described for intermediate I-4. Starting from intermediate I-1 (25.82 g, 184.25 mmol) and intermediate I-3 (47.16 g, 239.5 mmol), intermediate compound I-5 was obtained as a yellow oil (123 g, quant) which was used in the following step without further purification.

Intermediate 6 (I-6)

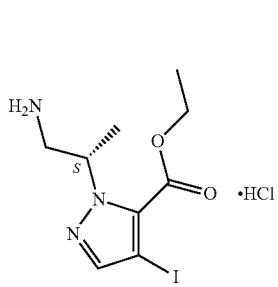

A 4M solution of HCl in 1,4-dioxane (10 mL, 40 mmol) was added to a solution of intermediate I-4 (4.2 g, 9.63 mmol) in acetonitrile (20 mL). The mixture was stirred at 80° C. for 2 h. The solvent was evaporated in vacuo to yield intermediate compound I-6 (3.5 g, 97%).

Intermediate 7 (I-7)

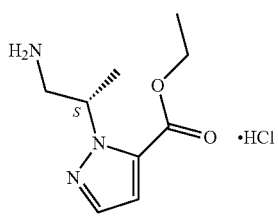

Intermediate compound I-7 was synthesized following a similar approach described for intermediate I-6. Starting from intermediate I-5 (54.79 g, 184.25 mmol) and a 4M solution of HCl in 1,4-dioxane (415 mL, 1.66 mol), intermediate compound I-7 was obtained as a white solid (32.5 g, 82% purity, 75%) which was used in the following step without further purification.

Intermediate 8 (I-8)

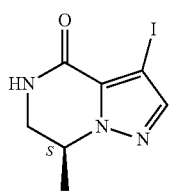

Intermediate I-6 as HCl salt (180 g, 350.4 mmol) was dissolved in a sat. sol. of NaHCO$_3$ (2 L). The mixture was stirred at rt for 12 h. The mixture was diluted with water and extracted with DCM. The organic layers were separated, dried (Na$_2$SO$_4$), filtered and the solvents evaporated in vacuo. Then the residue was washed with tert-butyl methyl ether to yield intermediate compound I-8 (92 g, 90%), mp 182.6-186.1° C. $^1$H NMR (500 MHz, DMSO-d$_6$) δ ppm 1.42 (d, J=6.65 Hz, 3H) 3.26-3.35 (m, 1H) 3.57-3.71 (m, 1H) 4.44-4.60 (m, 1H) 7.68 (s, 1H) 8.26 (br. s., 1H). LC-HRMS (ESI+) Calculated for C$_7$H$_8$IN$_3$O (M+H)$^+$: 277.9790, Found: m/z 277.9796 (+0.6 mDa), Rt=0.76 min (Method 13, see table 2). [α]=+11.7° (589 nm, c 1.00 w/v %, CH$_3$OH, 25° C.).

Intermediate 8a (I-8a)

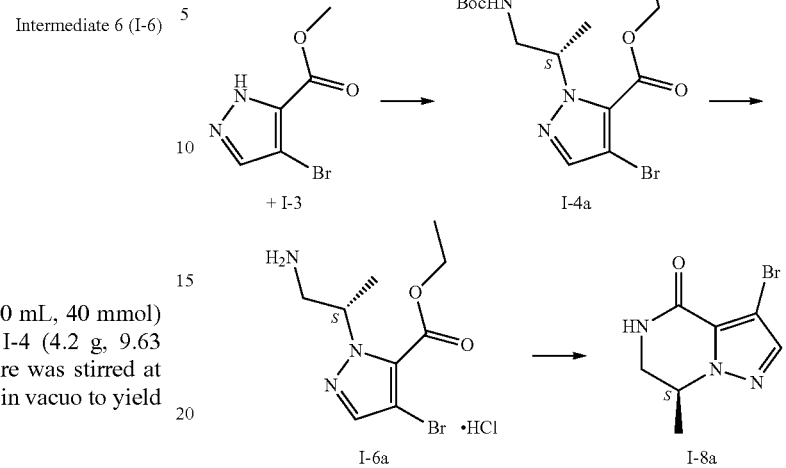

Intermediate 8a was prepared in 71% yield according to the following general description of a synthesis performed at a large scale:

A mixture of methyl 4-bromo-1H-pyrazole-5-carboxylate (referred to as "pyrazole SM" herein) (1 eq.), triphenyl phosphine (1.2 eq.), I-3 (1.2 eq.) and anhydrous THF (15 mL/g pyrazole SM) under nitrogen was cooled to 5-10° C. Di-tert-butyl azodicarboxylate (1.2 eq.) was added in portions at 5-15° C. under nitrogen. The solution was heated to 20-30° C. and stirred at 20-30° C. for 2-3 h. The obtained solution was concentrated and co-evaporated with isopropyl acetate to remove THF to afford a solution of crude 4-bromo-1-[(1S)-1-[[(1,1-dimethylethoxy)carbonyl]amino]ethyl]-1H-pyrazole-5-carboxylic acid methyl ester I-4a in isopropyl acetate (20 mL/g pyrazole SM). To the solution of I-4a was bubbled HCl gas at 15-30° C. until cleavage of the Boc protecting group was completed. The suspension was bubbled with nitrogen gas to remove most of the HCl gas. The suspension was concentrated to a volume of about 5 mL/g pyrazole SM below 50° C., and then isopropyl acetate (15 mL/g pyrazole SM) was added to the residue. Water (10 mL/g pyrazole SM) was added at 10-20° C. The mixture was stirred at 10-20° C. for 20-30 min. The mixture was filtered and the aqueous layer was separated. The organic layer was extracted with water (2 mL/g pyrazole SM). The combined aqueous layers were washed with isopropyl acetate (2×10 mL/g pyrazole SM) to remove residual triphenylphosphine oxide. I-6a was obtained as an aqueous solution (6.25 mL/g pyrazole SM). To the aqueous solution of I-6a was added potassium carbonate (~1 g/g pyrazole SM) to adjust to pH=8-9 at 10-25° C. The mixture was stirred at 10-25° C. for 5-6 h and solid I-8a precipitated. The suspension was cooled to 5-10° C. and stirred at 5-10° C. for 2-3 h, it was then filtered and washed with water (1 mL/g pyrazole SM) and heptanes (1 mL/g pyrazole SM), then dried in vacuo at 40-45° C. to afford I-8a as a white solid, mp. 196.12° C. $^1$H NMR (500 MHz, CDCl$_3$) δ ppm 1.61 (d, J=6.36 Hz, 3H) 3.48 (ddd, J=12.72, 7.22, 2.60 Hz, 1H) 3.75-3.84 (m, 1H) 4.49-4.59 (m, 1H) 6.54 (br. s., 1H) 7.56 (s, 1H). LC-HRMS (ESI+) Calculated for C$_7$H$_8$BrN$_3$O (M+H)$^+$: 229.9929, Found: m/z 229.9931 (+0.2 mDa), Rt=0.62 min (Method 13, see table 2). [α]=+25.2° (589 nm, c 0.53 w/v %, DMF, 20° C.).

Intermediate 9 (I-9)

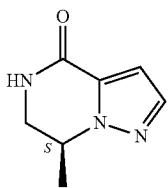

Intermediate compound I-9 was synthesized following a similar approach described for intermediate I-8. Starting from intermediate I-7 (32.5 g, 139.1 mmol), intermediate compound I-9 was obtained as a solid (14.8 g, 70%).

Intermediate 10 (I-10)

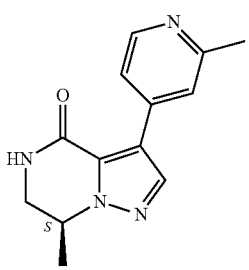

Pd(PPh$_3$)$_4$ (0.33 g, 0.29 mmol) was added to a stirred suspension of intermediate I-8 (1.6 g, 5.77 mmol) and 2-picoline-4-boronic acid (0.95 g, 6.93 mmol) in 1,4-dioxane (8 mL) and a sat. sol. of NaHCO$_3$ (4 mL) in a sealed tube under nitrogen. The mixture was stirred at 100° C. for 16 h. Then the mixture was diluted with H$_2$O and extracted with DCM. The organic layer was separated, dried (Na$_2$SO$_4$), filtered and the solvent evaporated in vacuo. The crude product was purified by flash column chromatography (silica; MeOH in DCM 0/100 to 6/94). The desired fractions were collected and the solvents evaporated in vacuo to yield intermediate compound I-10 as a white solid (1 g, 71%), mp 173.20° C. $^1$H NMR (500 MHz, CDCl$_3$) δ ppm 1.67 (d, J=6.65 Hz, 3H) 2.60 (s, 3H) 3.52 (ddd, J=12.79, 7.15, 2.89 Hz, 1H) 3.84 (dt, J=12.72, 4.00 Hz, 1H) 4.57-4.66 (m, 1H) 6.10 (br. s., 1H) 7.51 (dd, J=5.20, 1.44 Hz, 1H) 7.55 (s, 1H) 7.78 (s, 1H) 8.50 (d, J=5.20 Hz, 1H). LC-HRMS (ESI+) Calculated for C$_{13}$H$_{14}$IN$_4$O (M+H)$^+$: 243.1246, Found: m/z 243.1250 (+0.4 mDa), Rt=0.82 min (Method 13, see table 2). [α]=+32.8° (589 nm, c 0.52 w/v %, DMF, 20° C.).

Intermediate I-10 was alternatively prepared in 70% yield according to the following general description of a synthesis performed at a large scale:

A mixture of I-8a (1 eq.), 2-methyl-4-(4,4,5,5-tetramethyl-1,3,2-dioxaborolan-2-yl)-pyridine (1.1 eq.), anhydrous potassium phosphate (2 eq.), DME (7.5 mL/g I-13a) and purified water (2.5 mL/g I-13a) was evacuated and backfilled with nitrogen 3 times. Triphenyl phosphine (0.261 eq.) and palladium (II) acetate (0.131 eq.) were added in one portion under nitrogen. The mixture was evacuated and backfilled with nitrogen 3 times again, it was heated to 75-80° C. and stirred at 75-80° C. for 12-15 h under nitrogen. The aqueous layer was separated at 60-70° C. and discarded, and then water (8 mL/g I-13a) was added to the organic layer. DME was removed by concentration below 40° C. Isopropyl acetate (15 mL/g I-13a) was added, the pH of the mixture was adjusted to 1-2 with conc. HCl. The mixture was filtered and the filter cake was washed with water (1 mL/g I-13a), the aqueous layer was separated and the organic layer was extracted with water (2 mL/g I-13a). The combined aqueous layers were washed with Isopropyl acetate (2×15 mL/g I-13a). The aqueous layer was concentrated to remove residual DME and isopropyl acetate. MTBE (2 mL/g I-13a) was added and the mixture was cooled to 0-5° C., stirred at 0-5° C. for 2-3 h. I-10 was filtered, washed with cooled water (1 mL/g I-13a), and dried in vacuum at 45-50° C. to afford I-10 as an off-white solid.

Intermediate 11 (I-11)

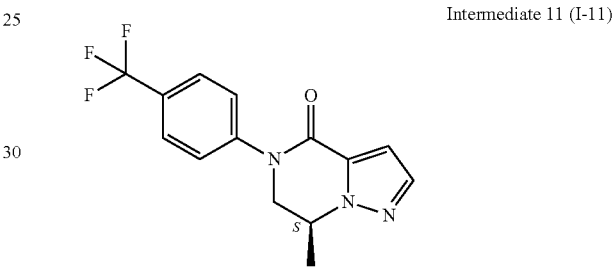

A mixture of intermediate I-9 (5 g, 33.01 mmol), copper (I) iodide (3.78 g, 19.85 mmol) and K$_2$CO$_3$ (9.14 g, 66.15 mmol) in toluene (150 mL) was nitrogen flushed for a few min. Then 4-bromobenzotrifluoride (9.3 mL, 66.1 mmol) and N,N'-dimethylethylenediamine (2.1 mL, 19.8 mmol) were added. The mixture was stirred under nitrogen at rt for 10 min and then stirred at 100° C. for 16 h. Then, DMF (20 mL) was added and the mixture was stirred at 100° C. for 8 h. Then water, a conc. sol. of ammonia and DCM were added. The organic layer was separated, dried (Na$_2$SO$_4$), filtered and the solvents evaporated in vacuo. The crude product was purified by flash column chromatography (silica; EtOAc in DCM 0/100 to 50/50). The desired fractions were collected and the solvents evaporated in vacuo to yield intermediate compound I-11 as a pale yellow oil (9.6 g, 98%).

In a procedure analogous to that described for intermediate I-11, the following intermediates were synthesized:

| Starting Material | Reagent | Intermediate Product |
|---|---|---|
| I-9 | Br-C$_6$H$_3$-Cl$_2$ (3,4-dichlorobromobenzene) | I-12 |
| | (solvent: toluene/DMF) | |

-continued

| Starting Material | Reagent | Intermediate Product |
|---|---|---|
| I-9 | 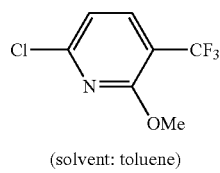<br>(solvent: toluene) | 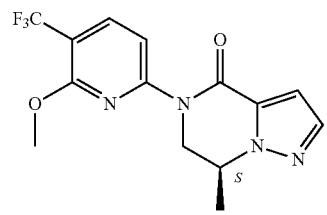<br>I-13 |
| I-9 | 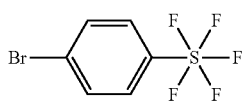 | 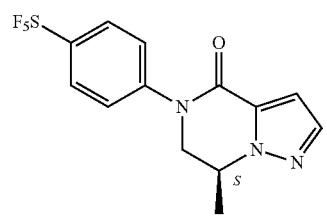<br>I-14 |

Intermediate 15 (I-15)

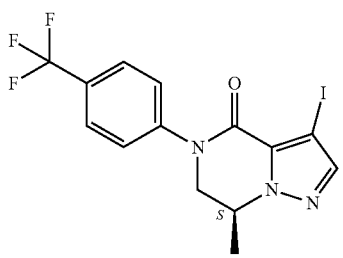

Iodine (11.55 g, 45.5 mmol) was added to a solution of intermediate I-11 (19.2 g, 65.0 mmol) and ammonium cerium(IV) nitrate (24.95 g, 45.5 mmol) in acetonitrile (350 mL). The mixture was stirred at 70° C. for 1 h. Then the mixture was diluted with EtOAc and washed with a sat. sol. of $Na_2S_2O_3$ and brine. The organic layer was separated, dried ($Na_2SO_4$), filtered and the solvents evaporated in vacuo. The residue was precipitated with DIPE and then was purified by short column chromatography (silica, DCM) then by flash column chromatography (silica; DCM in heptane 50/50 to 100/0). The desired fractions were collected and the solvents evaporated in vacuo to yield intermediate compound I-15 as a solid (24.8 g, 90%).

In a procedure analogous to that described for intermediate I-15, the following intermediates were synthesized:

| Starting Material | Intermediate Product |
|---|---|
| I-12 | 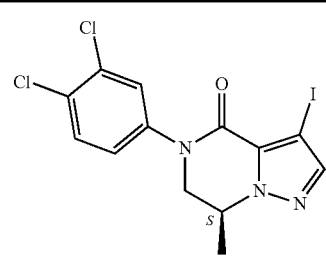<br>I-16 |
| I-13 | 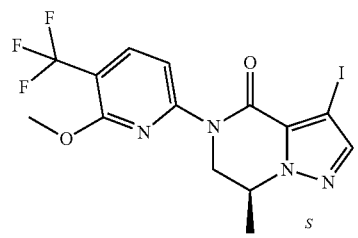<br>I-17 |
| I-14 | 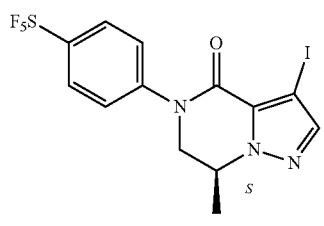<br>I-18 |

Intermediate 19 (I-19)

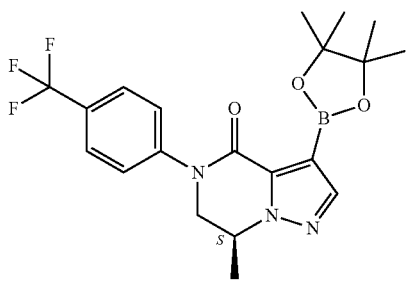

(I-19)

Isopropylmagnesium chloride lithium chloride complex (1.3M solution, 32.9 mL, 42.7 mmol) was added dropwise to a stirred solution of intermediate I-15 (10 g, 23.7 mmol) and 2-isopropoxy-4,4,5,5-tetramethyl-1,3,2-dioxaborolane (9.7 mL, 47.5 mmol) in anhydrous THF (100 mL) at −25° C. under nitrogen atmosphere. The mixture was stirred for 30 min at −25° C. Then the reaction was quenched with a 10% NH₄Cl aq sol. and extracted with EtOAc. The organic layer was separated, dried (Na₂SO₄), filtered and the solvents evaporated in vacuo. The crude product was purified by flash column chromatography (silica; MeOH in DCM 0/100 to 3/97). The desired fractions were collected and the solvents evaporated in vacuo. The crude product was triturated with DIPE, filtered and dried to yield intermediate compound I-19 (6.4 g, 64%) as a white solid. The solution and impure fractions from the column purification were combined and repurified by flash column chromatography (silica, EtOAc in Heptane 30/70 to 70/30). The desired fractions were collected and the solvents evaporated in vacuo. The product was triturated in DIPE/Heptane, filtered and dried to yield intermediate compound I-19 (1 g, 10%) as a white solid.

The following intermediates were synthesized by following an analogous synthetic procedure as reported for intermediate 19:

| Starting Material | Intermediate Product |
|---|---|
| I-16 | 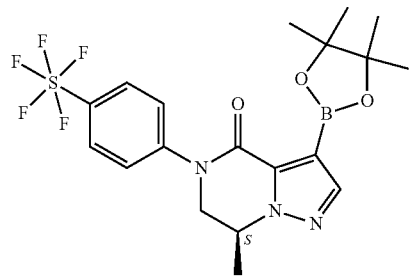<br>I-20 |

| Starting Material | Intermediate Product |
|---|---|
| I-17 | 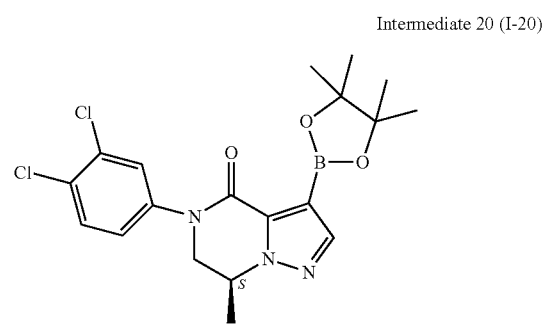<br>I-21 |

Alternative synthesis of

Intermediate 20 (I-20)

Two solutions of I-16 (250 mg, 0.592 mmol) and 2-isopropoxy-4,4,5,5-tetramethyl-1,3,2-dioxaborolane (0.242 mL, 1.185 mmol) in THF (1.5 mL) and isopropylmagnesium chloride-LiCl complex (1.3 M in THF, 820.17 µL, 1.066 mmol) in THF (1 mL) were pumped through a LTF mixer (0.5 mL/min), at 0° C., Rt=1 min. The mixture was collected over 4 mL of 10% NH₄Cl and extracted with EtOAc. The organic layer was separated, dried (Na₂SO₄), filtered and the solvent evaporated to yield I-20 (250 mg, quantitative) as a clear oil.

Intermediate 22 (I-22)

Two solutions of I-18 (1.57 g, 3.276 mmol) and 2-isopropoxy-4,4,5,5-tetramethyl-1,3,2-dioxoborolane (1.34 mL, 6.552 mmol) in THF (17.11 mL) and isopropylmagnesium chloride-LiCl complex (1.3 M in THF, 3.78 mL, 4.914 mmol) in THF (14.88 mL) were pumped through a LTF mixer (0.5 mL/min), at 0° C., R_f=1 min. The outlet solution was diluted with a solution of NH₄Cl and treated with EtOAc. The mixture was filtered through diatomaceous earth and the filtrate was extracted with EtOAc. The organic layer was separated, dried (Na₂SO₄), filtered and the solvents evaporated in vacuo. The residue was triturated with DIPE/heptane, filtered and dried to yield I-22 (1.23 g, 78.5%) as a white solid.

Intermediate 23 (I-23)

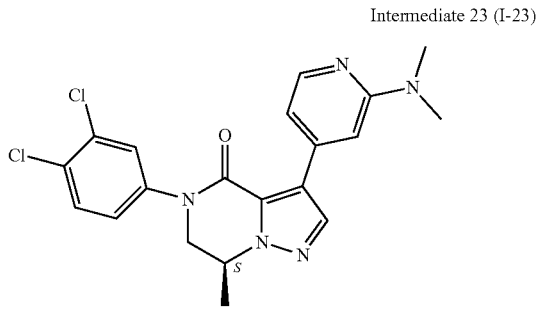

A solution of 4-bromo-2-(dimethylamino)pyridine (154.806 mg, 0.77 mmol) in THF (4.5 mL) and a solution of I-20 (250 mg, 0.592 mmol) in KOH (4.738 mL, 1.185 mmol) were pumped through an X-Terra® column filled with 0.5 g of Siliacat® DPP Pd (500 mg) using the Vapourtec R2+R4 reactor. (0.5 mL void volume, 0.05 mL/min each, 60° C., 5 min residence time). The outcome was collected. The mixture was diluted with water and extracted with CH₂Cl₂. The organic layer was separated, dried (Na₂SO₄), filtered and the solvent evaporated. The residue was purified by column chromatography (silica, EtOAc in CH₂Cl₂ 0/100 to 100/0). Desired fractions were collected and the solvent evaporated to yield I-23 (150 mg, 61%) as a clear oil.

Intermediate 24 (I-24)

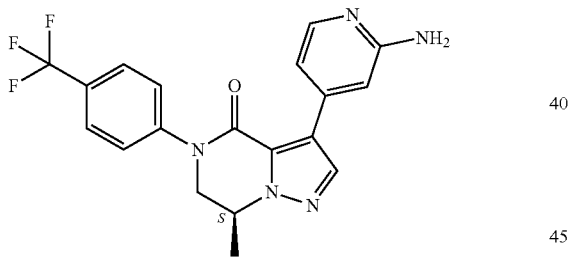

Pd(PPh₃)₄ (96 mg, 0.083 mmol) was added to a stirred suspension of intermediate I-15 (700 mg, 1.66 mmol) and 2-aminopyridine-4-boronic acid (458 mg, 3.32 mmol) in 1,4-dioxane (10 mL) and a sat. sol. of NaHCO₃ (5 mL). The mixture was stirred at 150° C. for 10 min under microwave irradiation. Then the mixture was diluted with H₂O and extracted with DCM. The organic layer was separated, dried (Na₂SO₄), filtered and the solvent evaporated in vacuo. The crude product was purified by flash column chromatography (silica; MeOH in DCM 0/100 to 10/90). The desired fractions were collected and the solvents evaporated in vacuo and the residue was purified by RP HPLC (RP C18 XBridge® 30×100 mm 5 μm), mobile phase (gradient from 67% 0.1% NH₄CO₃H/NH₄OH pH 9 solution in Water, 33% CH₃CN to 50% 0.1% NH₄CO₃H/NH₄OH pH 9 solution in Water, 50% CH₃CN). The residue was purified by ion exchange chromatography using an ISOLUTE® SCX2 cartridge eluting first with MeOH and then with 7M solution of ammonia in MeOH. The desired fractions contained in the 7M solution of ammonia in MeOH were collected and the solvents evaporated in vacuo to yield I-24 as a white solid (163 mg, 25%). ¹H NMR (500 MHz, CDCl₃) δ ppm 1.74 (d, J=6.4 Hz, 3H) 4.01 (dd, J=12.6, 7.1 Hz, 1H) 4.29 (dd, J=12.6, 4.2 Hz, 1H) 4.43 (br. s., 2H) 4.78 (quind, J=6.6, 4.3 Hz, 1H) 6.94 (dd, J=5.5, 1.4 Hz, 1H) 6.98 (s, 1H) 7.51 (br. d, J=8.4 Hz, 2H) 7.71 (br. d, J=8.4 Hz, 2H) 7.79 (s, 1H) 8.06 (d, J=4.9 Hz, 1H).

Intermediate 25 (I-25)

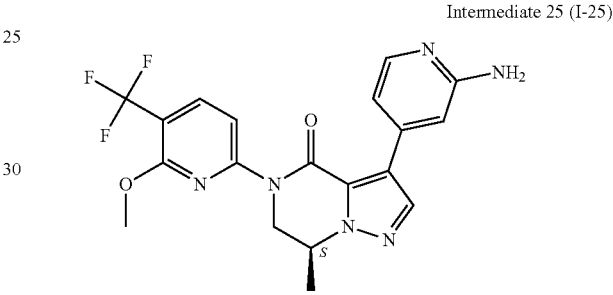

Pd(PPh₃)₄ (55.852 mg, 0.0483 mmol) was added to a stirred suspension of I-17 (437.093 mg, 0.967 mmol), 2-aminopyridine-4-boronic acid ([CAS903513-62-2], 200 mg, 1.45 mmol) and sat Na₂CO₃ (4.6 mL) in 1,4-dioxane (6.9 mL). The mixture was stirred at 150° C. for 10 min under microwave irradiation. Then the mixture was diluted with H₂O and extracted with DCM. The organic layer was dried over Na₂SO₄, filtered and the solvent evaporated in vacuo. The crude product was purified by flash column chromatography (silica; EtOAc in DCM 0/100 to 50/50). The desired fractions were collected and evaporated in vacuo, then triturated with DIPE and filtered to yield I-25 (143 mg, 35%).

The following intermediates were synthesized by following an analogous synthetic procedure as reported for intermediate 25:

| Intermediate | Starting Material | Reagent |
|---|---|---|
| I-26 (structure shown) | I-15 | 2-chloropyridine-4-boronic acid [458532-96-2] |

| Intermediate | Starting Material | Reagent |
| --- | --- | --- |
| 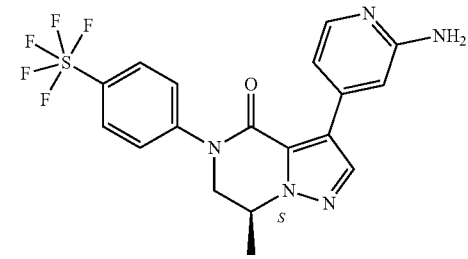<br>I-27 | I-18 | 2-aminopyridine-4-boronic acid [CAS903513-62-2] |

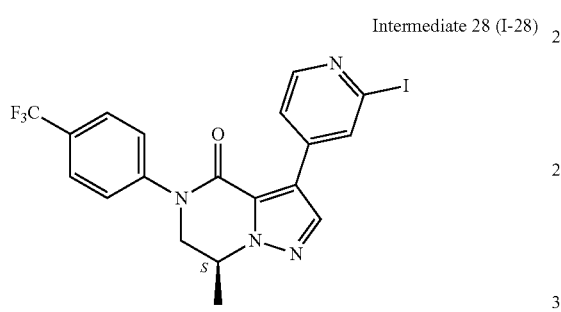

Intermediate 28 (I-28)

Acetyl chloride (84 µL, 1.18 mmol) was added to a stirred suspension of intermediate I-26 (320 mg, 0.786 mmol) and NaI (1.18 g, 7.866 mmol) in CH$_3$CN (12.8 mL) at rt. The mixture was stirred at 120° C. for 30 min under MW irradiation. Then the mixture was diluted with EtOAc and washed with a sat. sol. of Na$_2$S$_2$O$_3$ and brine. The organic layer was separated, dried (Na$_2$SO$_4$), filtered and the solvents evaporated in vacuo. The crude product was purified by flash column chromatography (silica; EtOAc in Heptane 0/100 to 60/40). The desired fractions were collected and evaporated in vacuo to yield I-28 (289 mg, 74%). $^1$H NMR (400 MHz, CDCl$_3$) δ ppm 1.75 (d, J=6.5 Hz, 3H) 4.02 (dd, J=12.8, 7.3 Hz, 1H) 4.30 (dd, J=12.7, 4.2 Hz, 1H) 4.80 (quind, J=6.7, 4.2 Hz, 1H) 7.50 (br. d, J=8.3 Hz, 2H) 7.67 (dd, J=5.1, 1.6 Hz, 1H) 7.72 (br. d, J=8.3 Hz, 2H) 7.80 (s, 1H) 8.03-8.05 (m, 1H) 8.32 (dd, J=5.2, 0.6 Hz, 1H).

B. Preparation of the Final Compounds

Example 1 (7S)-7-Methyl-3-(2-methylpyridin-4-yl)-5-[4-(trifluoromethyl)phenyl]-6,7-dihydropyrazolo[1,5-a]pyrazin-4(5H)-one (Co. No. 1)

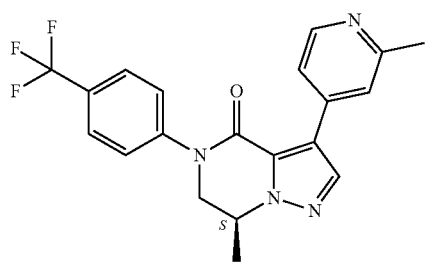

Procedure A: Copper(I) iodide (872 mg, 4.58 mmol) was added to a stirred suspension of intermediate I-10 (1.85 g, 7.64 mmol), 4-bromobenzotrifluoride (2.14 mL, 15.27 mmol), K$_2$CO$_3$ (2.11 g, 15.27 mmol) and N,N'-dimethylethylenediamine (0.492 mL, 4.58 mmol) in toluene (70 mL) in a sealed tube and under nitrogen. The mixture was stirred at 100° C. for 16 h. Then DMF (10 mL) was added and the mixture was stirred at 100° C. for additional 8 h. The mixture was filtered through diatomaceous earth and washed with EtOAc. The organic layer was washed with diluted NH$_4$OH sol, dried (Na$_2$SO$_4$), filtered and the solvents evaporated in vacuo. The crude product was purified by flash column chromatography (silica; EtOAc in Heptane 20/80 to 50/50). The desired fractions were collected and the solvents evaporated in vacuo. The product was precipitated with heptane, filtered and dried in vacuo to yield final product compound 1 as a white solid (2.32 g, 78%). $^1$H NMR (500 MHz, CDCl$_3$) δ ppm 1.75 (d, J=6.4 Hz, 3H), 2.57 (s, 3H), 4.02 (dd, J=12.7, 7.2 Hz, 1H), 4.30 (dd, J=12.6, 4.2 Hz, 1H), 4.75-4.84 (m, 1H), 7.44 (d, J=5.2 Hz, 1H), 7.49 (d, J=3.8 Hz, 2H), 7.51 (s, 1H), 7.71 (d, J=8.4 Hz, 2H), 7.80 (s, 1H), 8.48 (d, J=5.2 Hz, 1H).

Procedure B: Copper(I) iodide (94 mg, 0.495 mmol) was added to a stirred suspension of intermediate I-10 (200 mg, 0.825 mmol), 4-bromobenzotrifluoride (0.231 mL, 1.651 mmol), K$_2$CO$_3$ (228 mg, 1.65 mmol) and N,N'-dimethylethylenediamine (53 µL) in toluene (7.5 mL) in a sealed tube and under nitrogen. The mixture was stirred at 100° C. overnight. The mixture was filtered through a pad of diatomaceous earth and washed with DCM. The organic layer was separated, dried (MgSO$_4$), filtered and the solvents evaporated in vacuo. The crude product was purified by flash column chromatography (silica, EtOAc in Heptane 0/100 to 70/30). The desired fractions were collected and concentrated in vacuo to yield compound 1 (283 mg, 89%) as a pinkish solid.

Procedure C: Pd(PPh$_3$)$_4$ (384 mg, 0.332 mmol) was added to a stirred suspension of intermediate I-15 (2 g, 4.74 mmol) and 2-methylpyridine-4-boronic acid pinacol ester (1.66 g, 7.60 mmol) in 1,4-dioxane (10 mL) and a sat. sol. of Na$_2$CO$_3$ (5 mL) in a sealed tube under nitrogen. The mixture was stirred at 100° C. for 16 h. Then the mixture was diluted with H$_2$O and extracted with DCM and DCM with a small amount of EtOH. The organic layer was dried (Na$_2$SO$_4$), filtered and the solvent evaporated in vacuo. The crude product was purified by flash column chromatography (silica; 7M solution of ammonia in MeOH in DCM 0/100 to 3/97 then EtOAc in Heptane 0/100 to 100/0). The desired fractions were collected and evaporated in vacuo to yield compound 1 as a white solid (480 mg, 26%). (1.31 g of starting material was recovered).

Procedure D; general description of a synthesis performed at a large scale by which Co. No. 1 was isolated in 90% yield before purification:

A mixture of I-10 (1 eq.), potassium carbonate (2 eq.), copper(I) iodide (0.3 eq.), 4-bromobenzotrifluoride (1.3 eq.), N,N'-Dimethyl ethylenediamine (0.35 eq.), DMF (5 mL/g I-18) and toluene (8 mL/g I-18) was evacuated and backfilled with nitrogen 3 times. It was heated to 100-110° C. and stirred at 100-110° C. for 7-8 h under nitrogen.

The reaction solution was concentrated to remove toluene below 50° C. Isopropyl acetate (15 mL/g I-18) was added. The mixture was washed with 5% NH$_4$OH aqueous solution (3×7 mL/g I-18), and then 5% N-acetyl-L-cysteine and 5% K$_2$CO$_3$ aqueous solution (2×7 mL/g I-18) at 10-25° C. Finally, it was washed with 5% NaCl aqueous solution (5 mL/g I-18). The obtained solution was concentrated and co-evaporated with MTBE to remove isopropyl acetate. The resulting solid was filtered and dried in vacuo at 45-50° C. Co. No. 1 was obtained as an off-white solid which was further purified as follows:

Co. No. 1 was dissolved in a solvent mixture of IPA (4 mL/g Co. No. 1) and water (1 mL/g Co. No. 1) at 48-55° C. The solution was filtered and cooled to 0-5° C. An IPA/water mixture (0.5 mL/g Co. No. 1, 4/1 v/v) was used to rinse. Water (650 μL/g Co. No. 1) was added drop-wise and seeding with Co. No. 1 was performed. The mixture was stirred at 0-5° C. for 3-4 h. Water (14 mL/g Co. No. 1) was added drop-wise at 0-5° C. for 3-4 h, and then the suspension was stirred at 0-5° C. for 5-6 h. The wet product was filtered and rinsed with water (2 mL/g Co. No. 1), then dried in vacuo at 45-50° C. for 16 h to afford Co. No. 1 as a white solid.

For compound 1 (DSC mp=155.35° C.), the hydrochloride salt (.HCl) (DSC mp=decomposes above 200° C.); the sulfate salt (.H$_2$SO$_4$) (DSC mp=decomposes above 200° C.); the methane sulfonate salt (.CH$_3$SO$_3$H) (DSC mp=252° C.); and the maleate salt (.HO$_2$CCH═CHCO$_2$H-cis) (DSC mp=163° C.); wherein the mp were determined by DSC (Mettler Toledo Q2000 MDSC, heating from 25 to 350° C. at 10° C./min) were obtained following the procedure described below:

Compound 1 (1.5 g) in 9 mL of IPA or acetone (hydrochloride and sulfate salts were generated in acetone; methanesulfonate and maleate salts were generated in IPA) were stirred at 50° C. until all the solid was dissolved. The acid (1.1 mol equivalents) was added to the solution and the reaction mixture was further stirred for 2 h at 50° C., then cooled to 20° C. in 1 h and further stirred for 30 h at 20° C. The suspension was filtered and the solids were dried at 50° C. in a vacuum oven overnight.

Example 2 (7S)-7-Methyl-3-[2-(methylamino)-4-pyridyl]-5-[4-(trifluoromethyl)phenyl]-6,7-dihydropyrazolo[1,5-a]pyrazin-4-one (Co. No. 2)

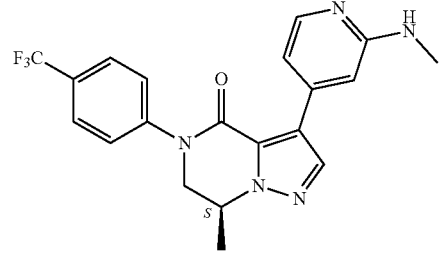

Pd(PPh$_3$)$_4$ (206 mg, 0.178 mmol) was added to a stirred suspension of I-19 (1.5 g, 3.561 mmol) and 4-bromo-N-methyl-pyridin-2-amine (799 mg, 4.273 mmol, 1.06 mmol) in a sat. sol. of NaHCO$_3$ (8.2 mL) and 1,4-dioxane (8.1 mL). The mixture was stirred at 120° C. for 10 minutes under microwave irradiation. The mixture was filtered through diatomaceous earth and washed with DCM. The organic layer was washed with water, separated, dried (Na$_2$SO$_4$), filtered and concentrated in vacuo. The residue was purified by flash column chromatography (silica; EtOAc in heptane 0/100 to 70/30). The desired fractions were collected and concentrated in vacuo to yield Co. No. 2, which was purified by RP HPLC (Stationary phase: C18 XBridge® 30×100 mm 5 μm, mobile phase: gradient from 67% 0.1% NH$_4$CO$_3$H/NH$_4$OH pH 9 solution in water, 33% CH$_3$CN to 50% 0.1% NH$_4$CO$_3$H/NH$_4$OH pH 9 solution in water, 50% CH$_3$CN), yielding Co. No. 2 (1.14 g, 80%) as a white solid. Co. No. 2 was triturated in heptane, yielding Co. No. 2 (181 mg, 13%) as a white solid. $^1$H NMR (500 MHz, CDCl$_3$) δ ppm 1.74 (d, J=6.4 Hz, 3H) 2.93 (d, J=5.2 Hz, 3H) 4.00 (dd, J=12.6, 7.1 Hz, 1H) 4.29 (dd, J=12.7, 4.0 Hz, 1H) 4.54 (br. d, J=3.2 Hz, 1H) 4.73-4.82 (m, 1H) 6.84 (s, 1H) 6.86 (d, J=5.2 Hz, 1H) 7.50 (br. d, J=8.4 Hz, 2H) 7.70 (br. d, J=8.4 Hz, 2H) 7.79 (s, 1H) 8.09 (d, J=5.2 Hz, 1H).

Example 3 (7S)-5-(3,4-Dichlorophenyl)-3-(2-fluoro-4-pyridyl)-7-methyl-6,7-dihydropyrazolo[1,5-a]pyrazin-4-one (Co. No. 3)

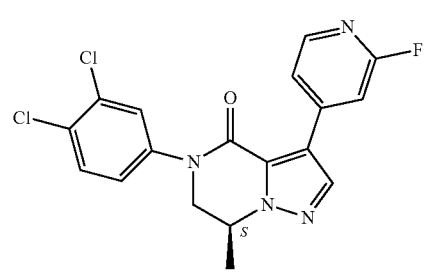

Pd(PPh$_3$)$_4$ (27.38 mg, 0.0237 mmol) was added to a stirred suspension of I-16 (200 mg, 0.474 mmol) and 2-fluoropyridine-4-boronic acid (1333.547 mg, 0.948 mmol) in 1,4-dioxane (2.8 mL, 32.829 mmol) and saturated Na$_2$CO$_3$ (1.4 mL). The mixture was stirred at 150° C. for 10 minutes under microwave irradiation. Then the mixture was diluted with H$_2$O and extracted with DCM. The organic layer was dried over Na$_2$SO$_4$, filtered and the solvent evaporated in vacuo. The crude product was purified by flash column chromatography (silica; EtOAc in DCM 0/100 to 20/80). The desired fractions were collected and evaporated in vacuo to yield Co. No. 3 (135 mg, 73%) as a yellow oil. Co. No. 3 was purified by RP HPLC (Stationary phase: C18 XBridge® 30×100 mm 5 μm), mobile phase: Gradient from 54% 0.1% $NH_4CO_3H/NH_4OH$ pH 9 solution in water, 46% $CH_3CN$ to 64% 0.1% $NH_4CO_3H/NH_4OH$ pH 9 solution in water, 36% $CH_3CN$), yielding Co. No. 3 (65 mg, 35%) as a solid. $^1$H NMR (400 MHz, $CDCl_3$) δ ppm 1.75 (d, J=6.5 Hz, 3H) 3.97 (dd, J=12.8, 7.3 Hz, 1H) 4.25 (dd, J=12.8, 4.3 Hz, 1H) 4.79 (quind, J=6.7, 4.2 Hz, 1H) 7.24 (dd, J=8.6, 2.5 Hz, 1H) 7.32-7.36 (m, 1H) 7.49 (d, J=2.3 Hz, 1H) 7.52 (d, J=8.6 Hz, 1H) 7.52-7.56 (m, 1H) 7.83 (s, 1H) 8.19 (d, J=5.3 Hz, 1H).

Example 4 (7S)-7-Methyl-3-[2-(methylamino)-4-pyridyl]-5-[4-(pentafluoro-λ$^6$-sulfanyl)phenyl]-6,7-dihydropyrazolo[1,5-a]pyrazin-4-one (Co. No. 4)

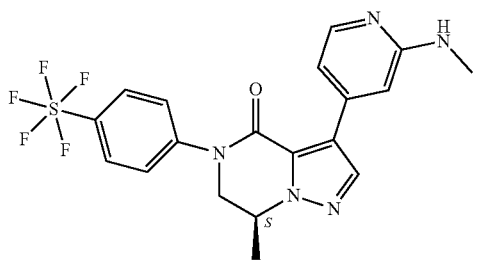

Pd(PPh$_3$)$_4$ (18.084 mg, 0.0156 mmol) was added to a stirred mixture of I-22 (150 mg, 0.313 mmol) and 4-bromo-N-methyl-2-pyridinamine (70.245 mg, 0.376 mmol) in NaHCO$_3$ sat sol (1.5 mL) and 1,4-dioxane (deoxygenated) (1.5 mL) under nitrogen. The mixture was stirred at 120° C. for 10 minutes under microwave irradiation. The mixture was diluted with water and extracted with ethyl acetate. The organic layer was separated, dried (Na$_2$SO$_4$), filtered and concentrated in vacuo. The crude product was purified by flash column chromatography (silica; EtOAc in DCM 0/100 to 100/0). The desired fractions were collected and concentrated in vacuo. Then the product was triturated with heptane/DIPE, filtered and dried to yield Co. No. 4 (110.4 mg, 77%) as a white solid. $^1$H NMR (500 MHz, CDCl$_3$) δ ppm 1.74 (d, J=6.6 Hz, 3H) 2.93 (d, J=5.2 Hz, 3H) 4.00 (dd, J=12.1, 6.9 Hz, 1H) 4.29 (dd, J=12.4, 4.0 Hz, 1H) 4.47-4.58 (m, 1H) 4.72-4.84 (m, 1H) 6.82 (s, 1H) 6.85 (dd, J=5.5, 1.3 Hz, 1H) 7.49 (d, J=8.7 Hz, 2H) 7.79 (s, 1H) 7.82 (d, J=9.2 Hz, 2H) 8.09 (d, J=5.2 Hz, 1H).

Example 5 (7S)-5-[6-Methoxy-5-(trifluoromethyl)-2-pyridyl]-7-methyl-3-[2-(methylamino)-4-pyridyl]-6,7-dihydropyrazolo[1,5-a]pyrazin-4-one (Co. No. 5)

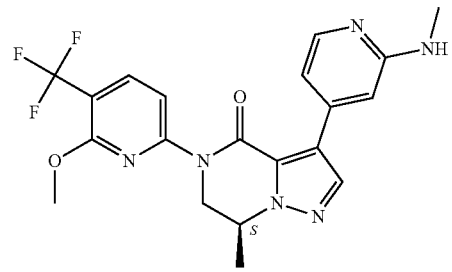

Pd(PPh$_3$)$_4$ (38.418 mg, 0.0332 mmol) was added to a stirred suspension of I-16 (300.657 mg, 0.665 mmol), 2-(methylamino)pyridin-4-ylboronic acid ([CAS 1214879-88-5], 151.561 mg, 0.997 mmol) and sat Na$_2$CO$_3$ (3 mL) in 1,4-dioxane (4.747 mL, 55.652 mmol). The mixture was stirred at 150° C. for 10 minutes under microwave irradiation. Then the mixture was diluted with H$_2$O and extracted with DCM. The organic layer was dried over Na$_2$SO$_4$, filtered and the solvent evaporated in vacuo. The crude product was purified by flash column chromatography (silica; EtOAc in DCM 0/100 to 50/50). The desired fractions were collected and evaporated in vacuo. The residue was precipitated with DIPE/heptane and evaporated to yield Co. No. 5 as a white solid. Co. No. 5 was purified by RP HPLC (Stationary phase: C18 XBridge® 30×100 mm 5 μm), Mobile phase: gradient from 60% 0.1% NH$_4$CO$_3$H/NH$_4$OH pH 9 solution in water, 40% CH$_3$CN to 43% 0.1% NH$_4$CO$_3$H/NH$_4$OH pH 9 solution in water, 57% CH$_3$CN), yielding Co. No. 5 (112 mg, 39%) as a white solid. $^1$H NMR (500 MHz, CDCl$_3$) δ ppm 1.72 (d, J=6.6 Hz, 3H) 2.96 (d, J=5.2 Hz, 3H) 4.05 (s, 3H) 4.42 (dd, J=13.6, 6.9 Hz, 1H) 4.52-4.60 (m, 1H) 4.64 (dd, J=13.6, 4.0 Hz, 1H) 4.69-4.78 (m, 1H) 6.76 (s, 1H) 6.84 (dd, J=5.2, 0.6 Hz, 1H) 7.77 (s, 1H) 7.78 (d, J=8.4 Hz, 1H) 7.88 (d, J=8.4 Hz, 1H) 8.13 (d, J=5.2 Hz, 1H).

C. Preparation of the Radioligand Precursors

Precursor 1 (P-1)

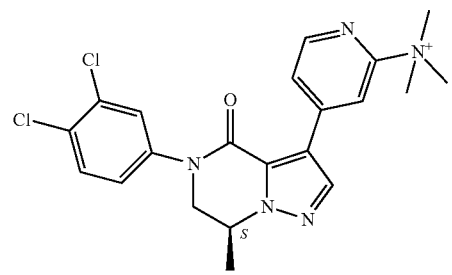

CH$_3$I (2.243 mL, 36.031 mmol) was added to a mixture of I-23 (150 mg, 0.36 mmol) and K$_2$CO$_3$ (1.867 g, 13.512 mmol) in MeOH (1.5 mL). The mixture was stirred at rt for 4 days. Then water and CH$_2$Cl$_2$ were added. The organic layer was separated with CH$_2$Cl$_2$, dried (Na$_2$SO$_4$), filtered and the solvent evaporated. The residue was triturated with EtOAc to yield P-1 (140 mg, 70%) as an off white solid. ¹H NMR (500 MHz, DMSO-d₆) δ ppm 1.60 (d, J=6.6 Hz, 3H) 3.59 (s, 9H) 4.06 (dd, J=13.0, 7.5 Hz, 1H) 4.36 (dd, J=13.0, 4.3 Hz, 1H) 4.83-4.93 (m, 1H) 7.49 (dd, J=8.7, 2.6 Hz, 1H) 7.75 (d, J=8.7 Hz, 1H) 7.81 (d, J=2.3 Hz, 1H) 8.10 (dd, J=4.9, 0.9 Hz, 1H) 8.28 (s, 1H) 8.43 (s, 1H) 8.63 (d, J=5.2 Hz, 1H).

Precursor 2 (P-2)

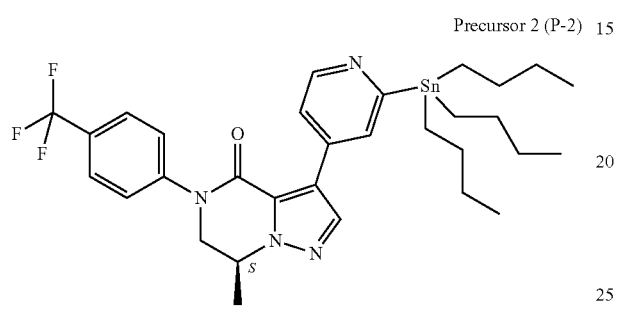

A solution of I-28 (700 mg, 1.405 mmol) and hexabutylditin (2137.233 μL, 4.2 mmol) in dry dioxane (15 mL) was bubbled with nitrogen for 5 min. Then Pd(PPh₃)₂Cl₂ (147.21 mg, 0.21 mmol) was added and the mixture was stirred at 163° C. for 17 min in a heated bath. Water and EtOAc were added and the phases were separated. The organic layer was dried over MgSO₄, filtered and concentrated. The crude was purified by reverse phase column chromatography (CH₃CN, ammonium acetate) to yield P-2 (191 mg, 20%). ¹H NMR (300 MHz, CDCl₃) δ ppm 8.65 (d, J=5.2 Hz, 1H), 7.72 (s, 1H), 7.66-7.53 (m, 3H), 7.51-7.35 (m, 3H), 4.80-4.65 (m, 1H), 4.23 (dd, J=4.1, 12.6 Hz, 1H), 3.95 (dd, J=7.1, 12.8 Hz, 1H), 1.68 (d, J=6.5 Hz, 3H), 1.64-1.36 (m, 6H), 1.35-1.15 (m, 6H), 1.15-0.93 (m, 6H), 0.92-0.72 (m, 9H).

Precursor 3 (P-3)

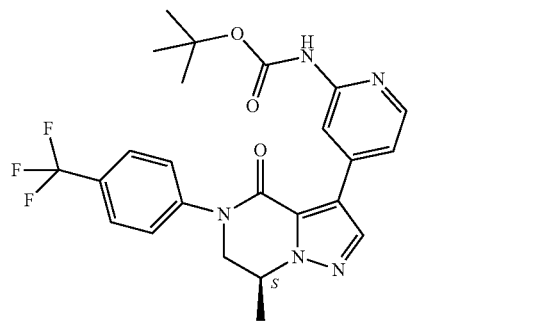

To a solution of di-tert-butyl dicarbonate (0.319 g, 1.462 mmol) in tBuOH (6 mL) was slowly added I-24 (515 mg, 1.329 mmol) in tBuOH (6 mL). This mixture was stirred for 20 h at 25° C. Then the solvent was evaporated and the crude product was purified by flash column chromatography (silica; MeOH in DCM 0/100 to 5/95). The desired fractions were collected and evaporated in vacuo to yield P-3 (430 mg, 66%) as a white solid. ¹H NMR (400 MHz, CDCl₃) δ ppm 1.52 (s, 9H) 1.74 (d, J=6.7 Hz, 3H) 4.01 (dd, J=12.7, 7.2 Hz, 1H) 4.31 (dd, J=12.7, 4.2 Hz, 1H) 4.73-4.83 (m, 1H) 7.39 (dd, J=5.3, 1.6 Hz, 1H) 7.50 (d, J=8.3 Hz, 2H) 7.58 (s, 1H) 7.69 (d, J=8.6 Hz, 2H) 7.85 (s, 1H) 8.13 (br. s, 1H) 8.22 (dd, J=5.3, 0.7 Hz, 1H).

The following precursors were synthesized by following an analogous synthetic procedure as reported for precursor 3:

| Starting Material | Precursor |
|---|---|
| I-28 | <br>P-4 |

| Starting Material | Precursor |
|---|---|
| I-25 | P-5 |

NMR P-4: $^1$H NMR (400 MHz, CDCl$_3$) δ ppm 1.52 (s, 9H) 1.73 (d, J=6.7 Hz, 3H) 4.01 (dd, J=12.7, 7.2 Hz, 1H) 4.30 (dd, J=12.7, 4.2 Hz, 1H) 4.72-4.84 (m, 1H) 7.37 (dd, J=5.1, 1.4 Hz, 1H) 7.48 (d, J=8.8 Hz, 2H) 7.64 (s, 1H) 7.82 (d, J=9.2 Hz, 2H) 7.84 (s, 1H) 8.13 (d, J=0.5 Hz, 1H) 8.22 (dd, J=5.3, 0.7 Hz, 1H).

NMR P-5: $^1$H NMR (500 MHz, CDCl$_3$) δ ppm 1.53 (s, 9H) 1.71 (d, J=6.6 Hz, 3H) 4.05 (s, 3H) 4.43 (dd, J=13.9, 7.2 Hz, 1H) 4.64 (dd, J=13.6, 4.0 Hz, 1H) 4.69-4.79 (m, 1H) 7.32 (dd, J=5.2, 1.4 Hz, 1H) 7.59 (s, 1H) 7.77 (d, J=8.4 Hz, 1H) 7.82 (s, 1H) 7.87 (d, J=8.1 Hz, 1H) 8.15 (s, 1H) 8.26 (d, J=5.2 Hz, 1H).

A. Preparation of Radioligands

Materials and Methods

High-performance liquid chromatography (HPLC) analysis was performed on a LaChrom Elite® HPLC system (Hitachi, Armstadt, Germany) connected to a UV spectrometer. For the analysis of radiolabeled compounds, the HPLC eluate, after passage through the UV detector, was led over a shielded 3-inch NaI(Tl) scintillation detector connected to a single channel analyser (Gabi box, Raytest, Straubenhardt, Germany). The output signal was recorded and analysed using a GINA Star data acquisition system (Raytest, Straubenhardt, Germany). Radioactivity in samples of biodistribution studies was quantified using an automated gamma counter equipped with a 3-inch NaI(Tl) well crystal coupled to a multichannel analyser (Wallac 2480 Wizard, Wallac, Turku, Finland). Results were corrected for background radiation, physical decay and counter dead time. Animals were housed in individually ventilated cages in a thermoregulated (~22° C.), humidity-controlled facility under a 12 h/12 h light/dark cycle with access to food and water ad libitum. All animal experiments were conducted according to the Belgian code of practice for the care and use of animals, after approval from the local University Ethics Committee for Animals.

a) Carbon-11 Labelled Tracers

[$^{11}$C]-2/[$^{11}$C]-4/[$^{11}$C]-5

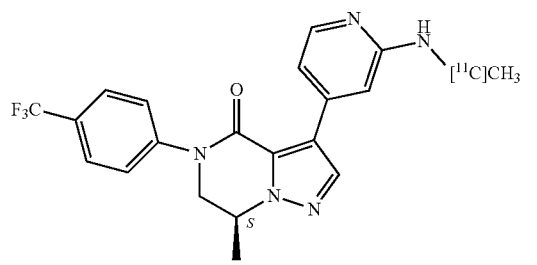

[$^{11}$C]-2

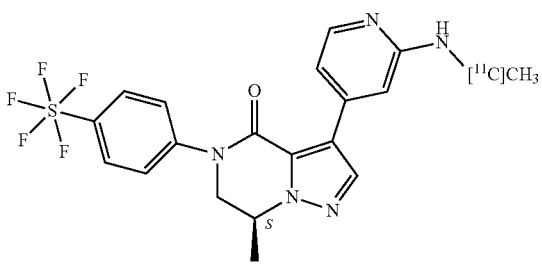

[$^{11}$C]-4

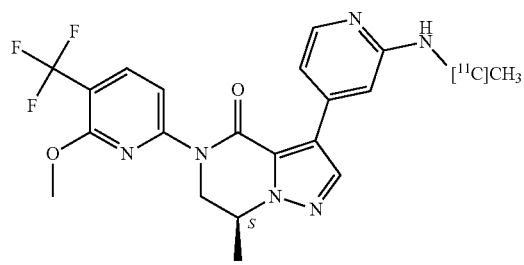

[$^{11}$C]-5

Carbon-11 was produced via a [$^{14}$N(p,α)$^{11}$C] nuclear reaction in a Cyclone 18/9 cyclotron (IBA, Louvain-la-Neuve, Belgium). The target gas, which is a mixture of N$_2$ (95%) and H$_2$ (5%), was irradiated using 18-MeV protons at a beam current of 25 μA. The irradiation was done for about 30 min to yield [$^{11}$C]methane ([$^{11}$C]CH$_4$). The [$^{11}$C]CH$_4$ was then transferred to a home-built recirculation synthesis module and trapped on a Porapak column that was immersed in liquid nitrogen. After flushing with helium, the condensed [$^{11}$C]CH$_4$ was converted to the gaseous phase by bringing the Porapak loop to room temperature. This [$^{11}$C]CH$_4$ was then reacted with vaporous I$_2$ at 650° C. to convert it to [$^{11}$C]methyl iodide ([$^{11}$C]MeI).

The resulting volatile [$^{11}$C]MeI was bubbled with a flow of helium through a solution of the N-Boc protected radiolabeling precursor P-3 (for [$^{11}$C]-2), P-5 (for [$^{11}$C]-5), and P-4 (for [$^{11}$C]-4) (0.5 mg) and NaH (~0.2 mg of a 60% dispersion in mineral oil) in anhydrous DMF (0.2 mL). When the amount of radioactivity in the reaction vial had stabilized, the reaction mixture was heated at 80° C. for 4 min. Deprotection was done by adding a 4M solution of HCl in 1,4-dioxane (0.2 mL) and heating the reaction mixture for 1 min at 100° C. After neutralization, the crude reaction mixture was injected onto an HPLC system consisting of a semi-preparative XBridge® column (C$_{18}$, 5 μm; 4.6 mm×150 mm; Waters, Milford, Mass., USA) that was eluted with a mixture of 0.01 M sodium phosphate buffer (pH 7.4) and EtOH (60:40 v/v) at a flow rate of 1 mL/min for [$^{11}$C]-2, with a mixture of 0.01 M sodium phosphate buffer (pH 7.4) and EtOH (55:45 v/v) at a flow rate of 0.8 mL/min for [$^{11}$C]-4 and with a mixture of 0.01 M sodium phosphate buffer (pH 2.2) and CH$_3$CN (60:40 v/v) at a flow rate of 0.8 mL/min for [$^{11}$C]-5. The radiolabeled product was collected between 15 and 17 min (small difference in retention time for the different tracers). The collected peak corresponding to the desired radioligand was then diluted with saline (Mini Plasco®, Braun, Melsungen, Germany) to obtain a final ethanol concentration of 10% and the solution was sterile filtered through 0.22 μm membrane filter (Millex®-GV, Millipore, Ireland). When CH$_3$CN was present in the preparative mobile phase, a post Cis SepPak purification was done prior to sterile filtration. The final formulation containing not more than 10% ethanol was then used for further in vitro and in vivo preclinical experiments. Quality control was performed using an analytical HPLC system consisting of an XBridge® column (C$_{18}$, 3.5 μm; 3 mm×100 mm; Waters) eluted with a mixture of 0.01 M sodium phosphate buffer (pH 9.6) and CH$_3$CN (65:35 v/v) at a flow rate of 0.6 mL/min and UV detection at 275 nm for [$^{11}$C]-2, with a mixture of 0.01 M sodium phosphate buffer (pH 9.6) and CH$_3$CN (60:40 v/v) at a flow rate of 0.6 mL/min and UV detection at 254 nm for [$^{11}$C]-4 and with a mixture of 0.01 M sodium phosphate buffer (pH 9.6) and CH$_3$CN (55:45 v/v) at a flow rate of 0.6 mL/min and UV detection at 217 nm for [$^{11}$C]-5. (Rt=6-10 min, small difference in retention time for the different tracers).

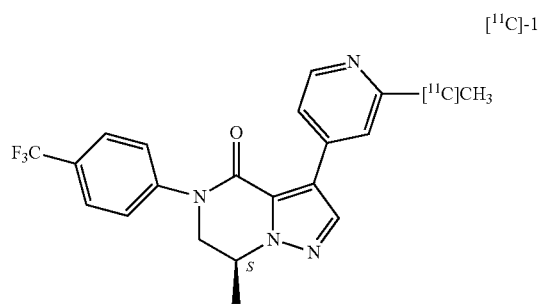

[$^{11}$C]-1

[$^{11}$C]MeI was bubbled with a flow of helium through a suspension of the Pd(PPh$_3$)$_4$ catalyst (2.6 μmol) in anhydrous DMF (0.2 mL, purged with N$_2$ prior to use) at room temperature for 2 min. A solution of P-2 (2.6 μmol) in anhydrous DMF (0.2 mL, purged with N$_2$ prior to use) was added and the reaction mixture was heated at 100° C. for 3 min. After dilution with a mixture of 0.01 M sodium phosphate buffer (pH 7.4) and EtOH (90:10 v/v), the catalyst was allowed to deposit for about 2 min after which the crude radiolabeling mixture was injected onto an HPLC system consisting of a semi-preparative XBridge® column (C$_{18}$, 5 μm; 4.6 mm×150 mm; Waters) that was eluted with a mixture of 0.01 M sodium phosphate buffer (pH 7.4) and EtOH (55:45 v/v) at a flow rate of 0.8 mL/min. [$^{11}$C]-1 was collected around 14 min and formulated as described hereinabove. Quality control was performed using an analytical HPLC system consisting of an XBridge® column (C$_{18}$, 3.5 μm; 3 mm×100 mm; Waters) eluted with a mixture of 0.05 M sodium acetate buffer (pH 5.5) and CH$_3$CN (65:35 v/v) at a flow rate of 0.6 mL/min and UV detection at 277 nm (Rt 10 min).

b) Fluorine-18 Labeled Tracers

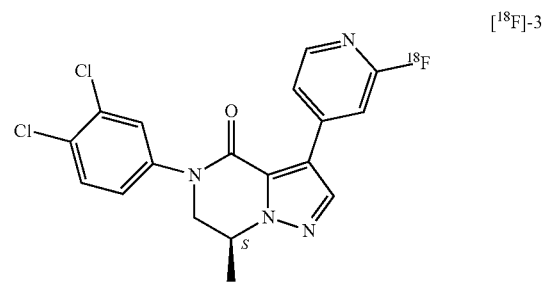

[$^{18}$F]-3

[$^{18}$F]fluoride ([$^{18}$F]F$^-$) was produced by an [$^{18}$O(p,n)$^{18}$F] nuclear reaction in a Cyclone 18/9 cyclotron (IBA, Louvain-la-Neuve, Belgium) by irradiation of 2 mL of 97% enriched [$^{18}$O]H$_2$O (Rotem HYOX18, Rotem Industries, Beer Sheva, Israel) using 18-MeV protons. After irradiation, the resultant [$^{18}$F]F$^-$ was separated from [$^{18}$O]H$_2$O using a Chromafix® (PS—HCO$_3$) anion exchange cartridge (Machery-Nagel, conditioned in the C$_2$O$_4^{2-}$ form). [$^{18}$F]F$^-$ was eluted from the cartridge using a solution containing K$_2$C$_2$O$_4$ (1.86 mg) and Kryptofix 222 (7.43 mg) dissolved in H$_2$O/CH$_3$CN (0.2 mL; 5:95 v/v).

The solution was evaporated under a stream of helium at 110° C. and further dried by azeotropic distillation using anhydrous CH$_3$CN (1 mL) under the same conditions until complete dryness. A solution P-1 (0.5 mg) in anhydrous CH$_3$CN (0.25 mL) was added to the dried [$^{18}$F]F$^-$/K$_2$C$_2$O$_4$/kryptofix complex and the mixture was heated at 82° C. for 2.5 min. Next, the crude radiolabeling mixture was diluted with a mixture of 0.05 M sodium acetate buffer (pH5.5) and EtOH (96:4 v/v) and injected onto an HPLC system consisting of a semi-preparative XBridge® column (C$_{18}$, 5 μm; 4.6 mm×150 mm; Waters) that was eluted with a mixture of 0.05 M sodium acetate buffer (pH5.5) and EtOH (60:40 v/v) at a flow rate of 0.8 mL/min. The radiolabeled product [$^{18}$F]-3 was collected after 49 min. Formulation was done as described higher. Quality control was performed using an analytical HPLC system consisting of an XBridge® column (C$_{18}$, 3.5 μm; 3 mm×100 mm; Waters) eluted with a mixture of 0.05 M sodium acetate buffer (pH 5.5) and CH$_3$CN (55:45 v/v) at a flow rate of 0.6 mL/min and UV detection at 221 nm (Rt 8.3 min).

[$^{11}$C]-2 was synthesized in 55% radiochemical yield (n=5),

[$^{11}$C]-5 was synthesized in 25% radiochemical yield (n=1),
[$^{11}$C]-4 was synthesized in 55% radiochemical yield (n=1),
[$^{11}$C]-1 was synthesized in 44% radiochemical yield (n=4),
[$^{18}$F]-3 was synthesized in 48% radiochemical yield (n=2), All yields were determined relative to starting [$^{11}$C]MeI or [$^{18}$F]F$^-$, non-decay corrected. All radioligands were obtained with radiochemical purity >95% and a specific radioactivity between 59 and 192 GBq/μmol as examined using the above described analytical HPLC systems.

The identity of the radiotracers was confirmed using the same analytical HPLC methods as described above after co-injection with their non-radioactive analogue.

II. Analytical Part

Melting Points

Values are peak values, and are obtained with experimental uncertainties that are commonly associated with this analytical method.

Mettler FP 62 (A):

For a number of compounds, melting points were determined in open capillary tubes on a Mettler FP62 apparatus. Melting points were measured with a temperature gradient of 3 or 10° C./minute. Maximum temperature was 300° C. The melting point was read from a digital display.

Mettler FP 81HT/FP90 (B):

For a number of compounds, melting points were determined in open capillary tubes on a FP 81HT/FP90 apparatus (Mettler-Toledo). Melting points were measured with a temperature gradient of 1, 3, 5 or 10° C./minute. Maximum temperature was 300° C. The melting point was read from a digital display.

DSC823e (C):

For a number of compounds, melting points (m.p.) were determined with a DSC823e (Mettler-Toledo) apparatus. Melting points were measured with a temperature gradient of 10° C./minute. Maximum temperature was 300° C. Peak values were recorded.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, [M+CH$_3$COO]$^-$ etc. . . . ). For molecules with multiple isotopic patterns (Br, Cl.), the reported value is the one obtained for the lowest isotope mass. All results were obtained with experimental uncertainties that are commonly associated with the method used.

TABLE 1

LC-MS Methods (Flow expressed in mL/min; column temperature (T) in ° C.; Run time in minutes).

| Method | Instrument | Column | Mobile phase | Gradient | Flow Col T | Run time |
|---|---|---|---|---|---|---|
| 1 | Agilent: HP1100-DAD, Waters: SQD | Agilent: Eclipse Plus C18 (3.5 μm, 2.1 × 30 mm) | A: 95% CH$_3$COONH$_4$ 6.5 mM + 5% CH$_3$CN, B: 1/1 CH$_3$CN/CH$_3$OH | 95% A kept for 0.2 min, to 0% A in 2.8 min, held for 0.15 min, back to 95% A in 0.15 min, held for 1.7 min | 1 60 | 5 |
| 2 | Waters: Acquity® UPLC®-DAD/SQD | Waters: CSH™ C18 (1.7 μm, 2.1 × 50 mm) | A: 95% CH$_3$COONH$_4$ 6.5 mM + 5% CH$_3$CN, B: CH$_3$CN | From 95% A to 5% A in 4.6 min, held for 0.4 min | 1 50 | 5 |
| 3 | Agilent: HP1100-DAD, Waters: LCT | Agilent: Eclipse Plus C18 (3.5 μm, 2.1 × 30 mm) | A: 95% CH$_3$COONH$_4$ 6.5 mM + 5% CH$_3$CN, B: CH$_3$CN/CH$_3$OH, 1/1 | From 95% A to 0% A in 5.0 min, held for 0.15 min, back to 95% A in 0.15 min, held for 1.7 min | 1 60 | 7 |
| 4 | Waters: Acquity® IClass UPLC®-DAD/Xevo G2-S QTOF | Waters: CSH™ C18 (1.7 μm, 2.1 × 50 mm) | A: 95% CH$_3$COONH$_4$ 6.5 mM + 5% CH$_3$CN, B: CH$_3$CN | From 95% A to 5% A in 4.6 min, held for 0.4 min | 1 50 | 5 |
| 5 | Waters: Acquity® UPLC®-DAD/SQD | Waters: CSH™ C18 (1.7 μm, 2.1 × 50 mm) | A: 95% CH$_3$COONH$_4$ 6.5 mM + 5% CH$_3$CN, B: CH$_3$CN | From 95% A to 40% A in 12 min, to 5% A in 0.6 min, held for 0.2 min | 1 50 | 2 |

TABLE 1-continued

LC-MS Methods (Flow expressed in mL/min; column temperature (T) in ° C.; Run time in minutes).

| Method | Instrument | Column | Mobile phase | Gradient | Flow | Col T | Run time |
|---|---|---|---|---|---|---|---|
| 6 | Agilent 1100-DAD-MSD G1956A | YMC-pack ODS-AQ C18 (50 × 4.6 mm, 3 μm) | A: 0.1% HCOOH in $H_2O$ B: $CH_3CN$ | From 95% A to 5% A in 4.8 min, held for 1.0 min, to 95% A in 0.2 min. | 2.6 | 35 | 6.0 |

TABLE 2

Analytical data - melting point (M.p.) and LCMS: [M + H]$^+$ means the protonated mass of the free base of the compound, [M − H]$^−$ means the deprotonated mass of the free base of the compound or the type of adduct specified [M + $CH_3COO$]$^−$). $R_t$ means retention time (in min). For some compounds, exact mass was determined.

| Co. No. | m.p. (° C.) | [M + H]$^+$ | [M − H]$^−$ or adduct | $R_t$ | LCMS Method |
|---|---|---|---|---|---|
| 1 | 152.6 (B) | 387 | 445 (M + $CH_3COO$)$^−$ | 2.73 | 1 |
| 2 | 85.9 (B) | 402 | 460 (M + $CH_3COO$)$^−$ | 2.01 | 2 |
| 3 | 170.3 (A, temp, grad.: 3° C./min) | 391 | 389 | 3.75 | 3 |
| 4 | n.d. | 460 | 518 (M + $CH_3COO$)$^−$ | 2.24 | 2 |
| 5 | 125.82 (C) | 433 | 431 | 2.34 | 2 |
| P-1 | n.d. | 430.1202 (+0.1 mDa) | — | 1.80 | 4 |
| P-2 | n.d. | 662 | — | 3.811 | 6 |
| P-3 | n.d. | 488 | 546 (M + $CH_3COO$)$^−$ | 1.44 | 5 |
| P-4 | 213.14 (C) | 546.1599 (+0.1 mDa) | — | 2.91 | 4 |
| P-5 | 198.32 and 208.33 (C) | 519.1967 (+0.0 mDa) | — | 3.06 | 4 |

Optical Rotations

Optical rotations were measured on a Perkin-Elmer 341 polarimeter with a sodium lamp and reported as follows: [α]° (λ, c g/100 ml, solvent, T° C.). $[α]_λ^T = (100α)/(l×c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 3

Optical Rotation data.

| Co. No. | $α_D$ (°) | Wavelength (nm) | Concentration w/v % | Solvent | Temperature (° C.) |
|---|---|---|---|---|---|
| 1 | +21.2 | 589 | 0.59 | DMF | 20 |
| 3 | +27.2 | 589 | 0.5 | DMF | 20 |
| 2 | +21.1 | 589 | 0.51 | DMF | 20 |
| 5 | +10.5 | 589 | 0.5 | DMF | 20 |
| 4 | +21.8 | 589 | 0.59 | DMF | 20 |
| P-4 | +19.1 | 589 | 0.6 | DMF | 20 |
| P-5 | +9.2 | 589 | 0.44 | DMF | 20 |

III. [$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein a subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the antagonist can be determined. mGlu2 receptors are shown to be preferentially coupled to Gal-protein, a preferential coupling for this method, and hence it is widely used to study receptor activation of mGlu2 receptors both in recombinant cell lines and in tissues. Here we describe the use of the [$^{35}$S]GTPγS binding assay using membranes from cells transfected with the human mGlu2 receptor and adapted from Schaffhauser et al. (Molecular Pharmacology, 2003, 4:798-810) for the detection of the negative allosteric modulation (NAM) properties of the compounds of this invention.

Membrane Preparation

CHO-cells were cultured to pre-confluence and stimulated with 5 mM butyrate for 24 h. Cells were then collected by scraping in PBS and cell suspension was centrifuged (10 min at 4000 RPM in benchtop centrifuge). Supernatant was discarded and pellet gently resuspended in 50 mM Tris-HCl, pH 7.4 by mixing with an Ultra Turrax homogenizer. The suspension was centrifuged at 12,400 RPM (Sorvall F14S-6×250Y) for 10 minutes and the supernatant discarded. The pellet was homogenized in 5 mM Tris-HCl, pH 7.4 using an Ultra Turrax homogenizer and centrifuged again (13,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 negative allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM $MgCl_2$ and 10 µM GDP. Human mGlu2 receptor-containing membranes were thawed on ice and diluted in assay buffer supplemented with 18 µg/ml saponin. Membranes were pre-incubated with compound together with a predefined (~$EC_{80}$) concentration of glutamate (60 µM) for 30 min at 30° C. After addition of [$^{35}$S]GTPγS (f.c. 0.1 nM), assay mixtures were shaken briefly and further incubated to allow [$^{35}$S]GTPγS incorporation on activation (30 minutes, 30° C.). Final assay mixtures contained 7 µg of membrane protein in 10 mM HEPES acid, 10 mM HEPES salt, pH 7.4, 100 mM NaCl, 3 mM $MgCl_2$, 10 µM GDP and 10 µg/ml saponin. Total reaction volume was 200 µl. Reactions were terminated by rapid filtration through Unifilter-96 GF/B plates (Perkin Elmer, Massachusetts, USA) using a 96-well filtermate universal harvester. Filters were washed 6 times with ice-cold 10 mM $NaH_2PO_4$/10 mM $Na_2HPO_4$, pH 7.4. Filters were then air-dried, and 30 µl of liquid scintillation cocktail (Microscint-O) was added to each well. Membrane-bound radioactivity was counted in a Topcount.

Data Analysis

The concentration-response curves of representative compounds of the present invention were generated using the Lexis software interface (developed at J&J). Data were calculated as % of the control glutamate response, defined as the response that is generated upon addition of an $EC_{80}$-equivalent concentration of glutamate. Sigmoid concentration-response curves plotting these percentages versus the log concentration of the test compound were analyzed using non-linear regression analysis. The concentration producing half-maximal inhibition was calculated as the $IC_{50}$.

The $pIC_{50}$ values were calculated as the $-\log IC_{50}$, when the $IC_{50}$ is expressed in M. $E_{max}$ is defined as the relative maximal effect (i.e. maximal % inhibition relative to the control glutamate response).

TABLE 4a

Pharmacological data for compounds according to the invention.

| Co. No. | GTPγS - hmGluR2 anGT $pIC_{50}$ | GTPγS - hmGluR2 anGT Emax |
|---|---|---|
| 1 | 8.05 | 105.51 |
| 3 | 8.26 | 106.95 |
| 2 | 8.24 | 105.535 |
| 5 | 8.5 | 111.16 |
| 4 | 8.52 | 105.7 |

TABLE 4b

Data in the [$^{35}$S]GTPγS binding assay and selectivity for mGluR2 versus mGluR1, mGluR3-mGluR8.

| Co. No. | GTPγS-hmGluR2 PAM $pEC_{50}$ | Selectivity over mGluR1, mGluR3-mGluR8 | | | | | |
|---|---|---|---|---|---|---|---|
| | | mGlu1 | mGlu3 | mGlu4 | mGlu5 | mGlu7 | mGlu8 |
| 1 | 8.05 | 1122.0 | 25.7 | 5623.4 | 1122.0 | 1122.0 | 1122.0 |
| 3 | 8.26 | 1819.7 | 16.2 | 9120.1 | 1819.7 | 1819.7 | 1819.7 |
| 2 | 8.24 | | 44.7 | 8709.6 | | | 1737.8 |
| 5 | 8.5 | | 234.4 | | | | |
| 4 | 8.52 | | 77.6 | | | | |

$pEC_{50}$ values were calculated from a concentration-response experiment of at least 8 concentrations. If more experiments were performed, the average $pEC_{50}$ value is reported and error deviation was <0.5.

IV. Biodistribution Studies

General Method

Biodistribution studies of [$^{11}$C]-2 and [$^{11}$C]-1 were carried out in healthy female Wister rats (body weight 185-220 g) at 2 min, 30 min and 60 min post injection (p.i.) (n=3/time point). Rats were injected with about 18 MBq of the tracer via a tail vein under anesthesia (2.5% isoflurane in $O_2$ at 1 L/min flow rate) and sacrificed by decapitation at the above specified time points. Blood and major organs were collected in tared tubes and weighed. The radioactivity in blood, organs and other body parts was measured using an automated gamma counter. For calculation of total blood radioactivity, blood mass was assumed to be 7% of the body mass. For calculation of total muscle and total bone radioactivity, muscle and bone mass were assumed to be 40% and 12% of the body mass, respectively.

Biodistribution Studies

[$^{11}$C]-2 and [$^{11}$C]-1

The results of the biodistribution study of [$^{11}$C]-2 and of [$^{11}$C]-1 in normal female Wistar rats is presented in Tables 5-10. Tables 5 and 6 show the % injected dose (% ID) values at 2 min, 30 min and 60 min post injection (p.i.) of [$^{11}$C]-2 and of [$^{11}$C]-1, respectively. For [$^{11}$C]-1 the 60 min time point was not studied.

TABLE 5

Biodistribution of [$^{11}$C]-2 in normal rats at 2, 30 and 60 min p.i.

| | % ID | | | | | |
|---|---|---|---|---|---|---|
| | Mean 2 min | SD 2 min | Mean 30 min | SD 30 min | Mean 60 min | SD 60 min |
| urine | 0.1 | 0.1 | 0.5 | 0.1 | 11 | 0.1 |
| kidneys | 5.3 | 0.7 | 2.2 | 0.2 | 1.6 | 0.1 |
| liver | 26.5 | 4.2 | 16.0 | 3.1 | 11.9 | 1.2 |
| spleen + pancreas | 2.4 | 0.1 | 1.4 | 0.2 | 1.1 | 0.3 |
| lungs | 6.8 | 4.7 | 1.8 | 0.1 | 1.3 | 0.3 |
| heart | 1.0 | 0.4 | 0.4 | 0.0 | 0.3 | 0.0 |
| intestines | 12.2 | 1.8 | 19.4 | 1.4 | 24.2 | 3.3 |
| stomach | 2.3 | 0.5 | 6.5 | 0.7 | 12.3 | 4.0 |
| striatum | 0.099 | 0.023 | 0.043 | 0.007 | 0.030 | 0.002 |
| hippocampus | 0.046 | 0.006 | 0.018 | 0.003 | 0.016 | 0.001 |
| cortex | 0.064 | 0.009 | 0.024 | 0.007 | 0.014 | 0.001 |
| rest of cerebrum | 0.944 | 0.139 | 0.323 | 0.020 | 0.256 | 0.028 |
| cerebrum total | 1.153 | 0.145 | 0.408 | 0.030 | 0.316 | 0.028 |
| cerebellum | 0.279 | 0.101 | 0.084 | 0.014 | 0.058 | 0.001 |
| blood | 4.9 | 0.9 | 2.8 | 0.5 | 2.0 | 0.1 |

TABLE 5-continued

Biodistribution of [¹¹C]-2 in normal rats at 2, 30 and 60 min p.i.

| | % ID | | | | | |
|---|---|---|---|---|---|---|
| | Mean 2 min | SD 2 min | Mean 30 min | SD 30 min | Mean 60 min | SD 60 min |
| carcass | 39.5 | 3.5 | 49.9 | 3.9 | 44.8 | 3.2 |
| bone | 7.0 | 2.4 | 4.9 | 0.8 | 4.2 | 0.5 |
| muscle | 11.1 | 2.2 | 24.1 | 3.9 | 21.4 | 2.8 |

Data are expressed as mean ± SD;
n = 3 per time point
% ID: Percentage of injected dose calculated as cpm in organ/total cpm recovered

TABLE 6

Biodistribution of [¹¹C]-1 in normal rats at 2 and 30 min p.i.

| | % ID | | | |
|---|---|---|---|---|
| | Mean 2 min | SD 2 min | Mean 30 min | SD 30 min |
| urine | 0.1 | 0.0 | 0.1 | 0.0 |
| kidneys | 2.9 | 0.1 | 1.6 | 0.4 |
| liver | 31.2 | 2.4 | 14.2 | 0.4 |
| spleen + pancreas | 1.9 | 0.4 | 1.2 | 0.0 |
| lungs | 2.1 | 0.8 | 0.9 | 0.1 |
| heart | 0.6 | 0.0 | 0.5 | 0.1 |
| intestines | 10.1 | 1.6 | 11.1 | 0.9 |
| stomach | 2.8 | 0.8 | 6.4 | 0.5 |
| striatum | 0.143 | 0.043 | 0.052 | 0.010 |
| hippocampus | 0.083 | 0.016 | 0.031 | 0.009 |
| cortex | 0.131 | 0.034 | 0.039 | 0.003 |
| rest of cerebrum | 1.286 | 0.153 | 0.445 | 0.030 |
| cerebrum total | 1.643 | 0.227 | 0.567 | 0.038 |
| cerebellum | 0.340 | 0.014 | 0.120 | 0.016 |
| blood | 6.3 | 0.3 | 3.4 | 0.1 |
| carcass | 43.4 | 3.9 | 61.5 | 1.8 |
| bone | 5.7 | 0.4 | 2.7 | 0.5 |
| muscle | 15.1 | 6.5 | 24.9 | 1.0 |

Data are expressed as mean ± SD;
n = 3 per time point
% ID: Percentage of injected dose calculated as cpm in organ/total cpm recovered Both tracers were cleared mainly via the liver into the intestines and partly via the renal pathway. High uptake was also observed in the carcass and the muscle however they constitute a large percentage of the body mass.

The total initial brain uptake of both tracers was relatively high with 1.4% ID and 2.0% ID at 2 min pi for [¹¹C]-2 and [¹¹C]-1, respectively (see table 7). Washout from brain was observed.

TABLE 7

Comparative total brain uptake in normal rats at 2, 30 (and 60 min) p.i. for [¹¹C]-2 and [¹¹C]-1

| | Total brain uptake (% ID, n = 3) | | |
|---|---|---|---|
| Compound | 2 min p.i. | 30 min p.i. | 60 min p.i. |
| [¹¹C-1] | 2.01 ± 0.24 | 0.69 ± 0.05 | / |
| [¹¹C-2] | 1.44 ± 0.24 | 0.50 ± 0.05 | 0.38 ± 0.03 |

Data are expressed as mean ± SD;
n = 3 per time point
% ID: Percentage of injected dose calculated as cpm in (cerebrum + cerebellum)/total cpm recovered Tables 8 and 9 present the radioactive concentration in the different brain regions, blood, bone and muscle for both tracers. These concentrations are expressed as standardized uptake values (SUV) and are corrected for body weight of the animal.

TABLE 8

[¹¹C]-2 concentration in different rat brain regions, blood, bone and muscle at 2, 30 and 60 min p.i. normalized for the body weight of the animal.

| | SUV | | | | | |
|---|---|---|---|---|---|---|
| | Mean 2 min | SD 2 min | Mean 30 min | SD 30 min | Mean 60 min | SD 60 min |
| striatum | 1.68 | 0.18 | 0.65 | 0.11 | 0.49 | 0.03 |
| hippocampus | 1.49 | 0.14 | 0.64 | 0.09 | 0.49 | 0.03 |
| cortex | 2.23 | 0.35 | 0.74 | 0.05 | 0.58 | 0.08 |
| rest of cerebrum | 1.79 | 0.13 | 0.66 | 0.11 | 0.49 | 0.04 |
| whole cerebrum | 1.79 | 0.14 | 0.66 | 0.10 | 0.49 | 0.04 |
| cerebellum | 1.78 | 0.02 | 0.62 | 0.12 | 0.45 | 0.02 |
| blood | 0.70 | 0.13 | 0.40 | 0.07 | 0.29 | 0.01 |
| cerebrum + cerebellum | 1.80 | 0.11 | 0.67 | 0.11 | 0.49 | 0.03 |
| bone | 0.59 | 0.20 | 0.44 | 0.04 | 0.37 | 0.04 |
| muscle | 0.26 | 0.07 | 0.56 | 0.06 | 0.48 | 0.06 |

Data are expressed as mean ± SD;
n = 3 per time point;
SUV: Standard uptake values are calculated as (radioactivity in cpm in organ/weight of the organ in g)/(total counts recovered/body weight in g)

TABLE 9

[¹¹C]-1 concentration in different rat brain regions, blood, bone and muscle at 2 and 30 min p.i. normalized for the body weight of the animal.

| | SUV | | | |
|---|---|---|---|---|
| | Mean 2 min | SD 2 min | Mean 30 min | SD 30 min |
| striatum | 2.58 | 0.32 | 0.97 | 0.02 |
| hippocampus | 2.41 | 0.13 | 0.87 | 0.01 |
| cortex | 3.51 | 0.31 | 1.09 | 0.02 |
| rest of cerebrum | 2.83 | 0.13 | 0.94 | 0.01 |
| whole cerebrum | 2.83 | 0.15 | 0.95 | 0.01 |
| cerebellum | 2.60 | 0.07 | 0.90 | 0.03 |
| blood | 0.90 | 0.04 | 0.49 | 0.02 |
| cerebrum + cerebellum | 2.82 | 0.12 | 0.95 | 0.01 |
| bone | 0.48 | 0.03 | 0.23 | 0.05 |
| muscle | 0.38 | 0.16 | 0.62 | 0.03 |

Data are expressed as mean ± SD;
n = 3 per time point;
SUV: Standard uptake values are calculated as (radioactivity in cpm in organ/weight of the organ in g)/(total counts recovered/body weight in g)

Significant wash-out from all studied brain regions was observed from 2 min to 30 min pi for both tracers and also further from 30 to 60 min p.i. for [¹¹C]-2 (not analyzed for [¹¹C]-1). The wash-out ratios are presented in table 10. Washout from blood and bone was slower. Some retention was observed in the muscle.

TABLE 10

Radioactivity washout from different rat brain regions, blood, bone and muscle calculated a 2 min - to- 30 min wash-out ratio for [¹¹C]-1 and [¹¹C]-2.

| | ¹¹C-1 | ¹¹C-2 |
|---|---|---|
| striatum | 2.68 | 2.59 |
| hippocampus | 2.76 | 2.31 |
| cortex | 3.22 | 3.04 |
| rest of cerebrum | 3.00 | 2.71 |
| whole cerebrum | 2.98 | 2.70 |
| cerebellum | 2.90 | 2.85 |
| blood | 1.86 | 1.75 |
| bone | 2.11 | 1.34 |
| muscle | 0.61 | 0.46 |

The washout from brain was slightly slower for [$^{11}$C]-2 compared to [$^{11}$C]-1. Highest washout ratio was observed for the cortex.

Washout from bone and blood from 2 to 30 min was faster for [$^{11}$C]-1 compared to [$^{11}$C]-2. For both tracers some retention was observed in the muscle.

The results of these biodistribution studies show that [$^{11}$C]-2 and [$^{11}$C]-1 have a relatively high initial brain uptake at 2 min post tracer injection but significant washout from brain is observed from 2 to 30 min. The brain uptake of [$^{11}$C]-2 was lower compared to that of [$^{11}$C]-1 but the washout from brain from 2 to 30 min was slightly slower for [$^{11}$C]-2 compared to [$^{11}$C]-1. The 2 min-to-30 min wash-out ratios were >2.3 for all studied brain regions with the highest ratio for the cortex.

V. In Vitro Autoradiography Binding Studies

General Method

In vitro autoradiography studies were performed on horizontal sections of mGluR2 KO and WT mouse brain and of normal female Wistar rat brain (20 µm). The sections were preincubated in 50 mM Tris-HCl (MgCl$_2$ 2 mM, CaCl$_2$ 2 mM; pH 7.0) for 10 min (two times) at room temperature and dried. Next, the brain sections were incubated with tracer [$^{11}$C]-2, [$^{11}$C]-5, [$^{11}$C]-4, [$^{11}$C]-1 or [$^{18}$F]-3 diluted in the same Tris-HCl buffer as used for the preincubation additionally containing 0.1% BSA or with this tracer solution in the presence of 10 µM Co. No. 2 or Co. No. 1. The mouse brain sections were incubated with 17 kBq of carbon-11 labeled tracer and 1.7 kBq of fluorine-18 labeled tracer. For the rat brain sections this was 44 kBq of carbon-11 labeled tracer and 0.44 kBq of fluorine-18 labeled tracer. After 30 min of incubation, the brain sections were washed three times for 5 min in ice-cold Tris-HCl 50 mM ((MgCl$_2$ 2 mM, CaCl$_2$ 2 mM; pH 7.0+0.1% BSA buffer). After a quick dip in purified ice-cold water, the slides were dried. Autoradiograms were obtained by exposing the slides overnight to a high-performance phosphor storage screen (super-resolution screen; Perkin Elmer, Waltham, USA). The screens were read using a Cyclone Plus system (Perkin Elmer) and analysed using Optiquant software (Perkin Elmer). The radioactivity concentration in the autoradiograms was expressed in digital light units (DLU)/mm$^2$.

In Vitro Autoradiography Binding Studies

To obtain additional information on the specificity of the tracer binding to mGluR2, in vitro autoradiography binding studies were performed on mGluR2 KO and WT mouse brain sections and on normal rat brain sections in presence or absence of a high concentration of mGluR2 NAM compounds (Co. No. 1 or Co. No. 2).

FIGS. 1-5 show the result of these binding studies on the mGluR2 KO and WT mouse brain sections for [$^{11}$C]-2, [$^{11}$C]-1, [$^{18}$F]-3, [$^{11}$C]-5 and [$^{11}$C]-4. Table 11 presents the 'WT total binding-to-KO total binding' ratio's and the 'WT total binding-to-WT blocked' ratio's for striatum and cortex of the five studied tracers.

TABLE 11

'WT total binding- to -KO total binding' ratio's and the 'WT total binding- to-WT blocked' ratio's for striatum and cortex for all five studied tracers

| Co. No. | Striatum WT (TB)/Striatum KO (TB) | Cortex WT (TB)/Cortex KO (TB) | Striatum WT (TB)/striatum WT (block Co. No. 1) | Cortex WT (TB)/cortex WT (block Co. No. 1) |
|---|---|---|---|---|
| [$^{11}$C]-2 | ~4.8 | ~8.1 | ~8.3 (~88% spec binding) | ~6.7 (~85% spec binding) |
| [$^{11}$C]-1 | ~3.8 | ~7.1 | ~11.8 (~92% specific binding) | ~21.5 (~95% spec binding) |
| [$^{11}$C]-5 | ~1.9 | ~2.6 | ~1.9 (~47% spec binding) | ~2.4 (~58% spec binding) |
| [$^{11}$C]-4 | ~2.2 | ~2.6 | ~2.6 (~62% spec binding) | ~3.8 (~74% spec binding) |
| [$^{18}$F]-3 | Higher binding to WT sections was not observed for all WT sections included in the study. Binding pattern differed from slice to slice | | | |

For [$^{11}$C]-2 and [$^{11}$C]-1 significant difference in tracer binding to WT mouse brain section and mGluR2 KO mouse brain section was observed. This binding to the WT mouse brain was heterogeneously with higher binding to striatum and cortex and this could be blocked with Co. No. 1 (10 µM) for more than ~85%. For [$^{11}$C]-5 and [$^{11}$C]-4 this difference in binding between WT and KO mouse brain was less pronounced and for [$^{18}$F]-3 no significant and consistent difference was observed.

The total binding to mGluR2 KO mouse brain was slightly higher for [$^{11}$C]-1 compared to [$^{11}$C]-2.

Figure 6:
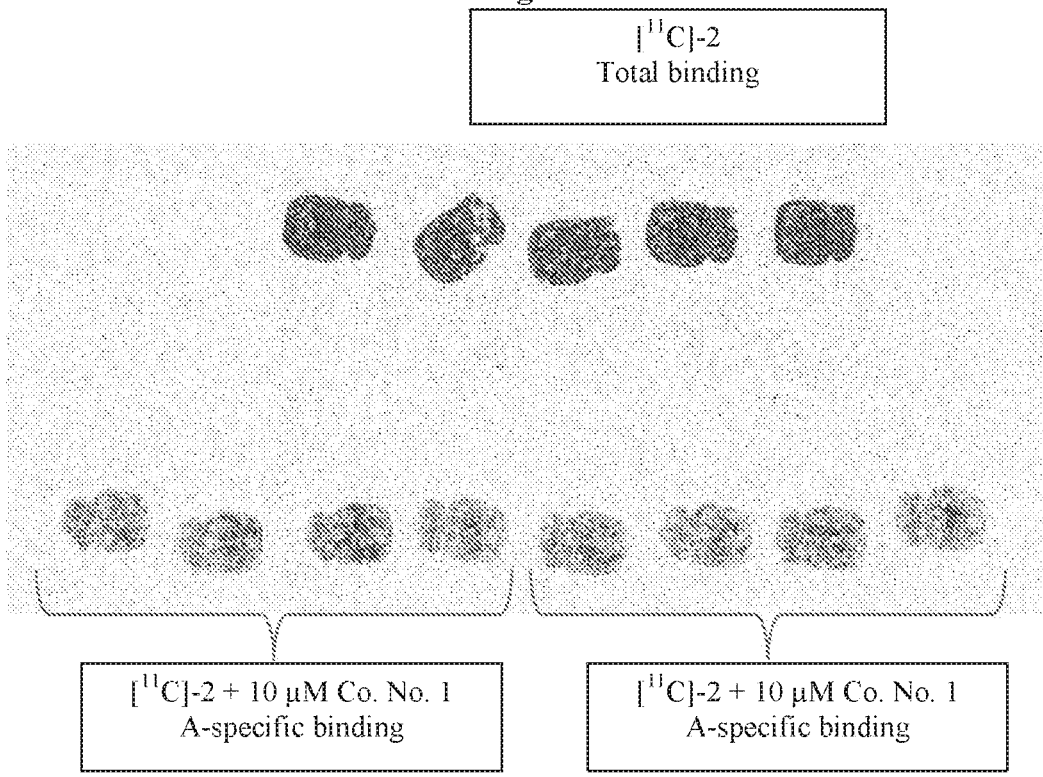
FIG. 6 shows the binding of [$^{11}$C]-2 to normal female rat brain sections. Total tracer binding is presented in the upper row; A-specific binding in presence of 10 μM of Co. No. 1 and in presence of 10 μM Co. No. 2 (self-block) is presented in the lower row.
Figure 7:
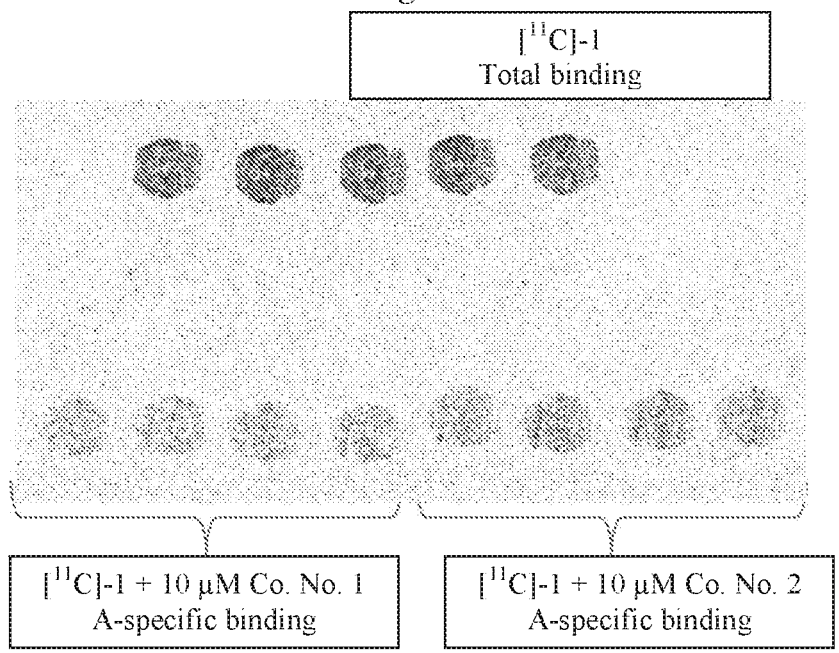
FIG. 7 shows the binding of [$^{11}$C]-1 to normal female rat brain sections. Total tracer binding is presented in the upper row; a-specific binding in presence of 10 μM of Co. No. 1 (self-block) and in presence of 10 μM Co. No. 2 is presented in the lower row.
Figure 8:
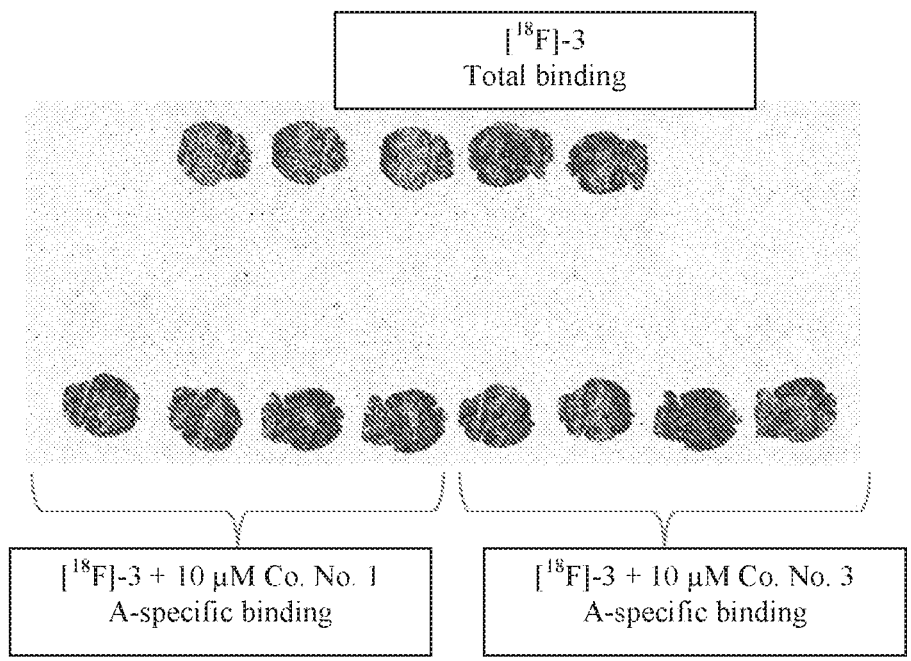
FIG. 8 shows the binding of [$^{18}$F]-3 to normal female rat brain sections. Total tracer binding is presented in the upper row; a-specific binding in presence of 10 μM of Co. No. 1 and in presence of 10 μM Co. No. 3 (self-block) is presented in the lower row.

For [$^{11}$C]-2, [$^{11}$C]-1 and [$^{18}$F]-3, the specificity of tracer binding was also studied in normal rat brain sections. The results of these binding studies are presented in FIGS. 6-8.

As was also observed for the WT mouse brain sections, high binding of [$^{11}$C]-2 was observed to striatum and cortex of normal rat brain in vitro. Self-blocking or blocking with Co. No. 1 (10 µM) resulted in a decrease in binding of ~78% in rat striatum and ~91% in rat cortex. These percentages are comparable to those obtained in the in vitro WT mouse brain binding studies.

In general, the total binding to rat brain was less pronounced for [$^{11}$C]-1 compared to [$^{11}$C]-2. For [$^{11}$C]-1, apart from striatum and cortex, binding to thalamus and colliculus was also observed which was not the case to the WT mouse brain sections.

When looking at the total binding of [$^{18}$F]-3 to rat brain, the distribution of the tracer throughout the brain differed from section to section. This was also observed in the WT mouse brain sections. Also the a specific binding to rat brain was higher for [$^{18}$F]-3 compared to that observed for [$^{11}$C]-2 and [$^{11}$C]-1.

Of all five tracers that were studied in the in vitro autoradiography binding experiments on mGluR2 KO and WT mouse brain sections and normal rat brain sections, [$^{11}$C]-2 had the highest percentage of specific binding (block with Co. No. 1) in the WT mouse brain, the highest WT total binding-to-KO total binding ratio for striatum and cortex, and showed the strongest binding to normal rat striatum and cortex.

The invention claimed is:
1. A compound having the Formula (P-3):

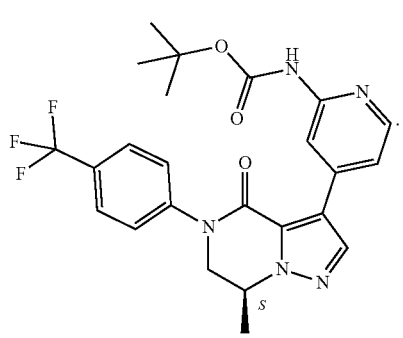

(P-3)

2. A process for the preparation of a compound of formula [$^{11}$C]-2:

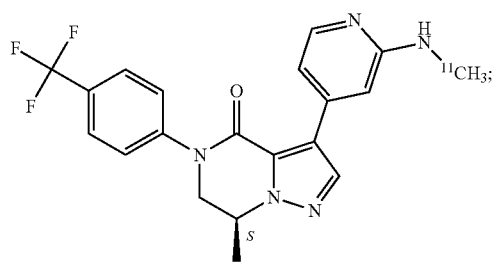

or a pharmaceutically acceptable salt thereof, comprising reacting a compound according to formula (P-3):

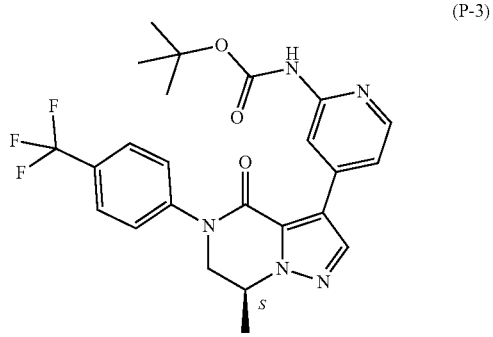

(P-3)

with [$^{11}$C]CH$_3$I under appropriate conditions, followed by Boc cleavage under appropriate conditions, to yield the compound of formula [$^{11}$C]-2.

* * * * *